United States Patent
Ewert et al.

(10) Patent No.: US 8,785,176 B2
(45) Date of Patent: Jul. 22, 2014

(54) POST PROTEIN HYDROLYSIS REMOVAL OF A POTENT RIBONUCLEASE INHIBITOR AND THE ENZYMATIC CAPTURE OF DNA

(71) Applicant: University of South Florida, Tampa, FL (US)

(72) Inventors: Matt Ewert, St. Petersburg, FL (US); Philip Amuso, Tampa, FL (US); Andrew Cannons, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 13/734,367

(22) Filed: Jan. 4, 2013

(65) Prior Publication Data

US 2013/0130234 A1   May 23, 2013

Related U.S. Application Data

(60) Continuation of application No. 13/725,924, filed on Dec. 21, 2012, which is a continuation of application No. 12/117,505, filed on May 8, 2008, which is a division of application No. 11/035,667, filed on Jan. 14, 2005, now Pat. No. 7,416,843, which is a continuation-in-part of application No. 10/604,779, filed on Aug. 15, 2003, now Pat. No. 7,998,699, said application No. 11/035,667 is a continuation-in-part of application No. PCT/US2004/026606, filed on Aug. 16, 2004, which is a continuation of application No. 10/604,779, filed on Aug. 15, 2003, now Pat. No. 7,998,699.

(60) Provisional application No. 60/319,474, filed on Aug. 15, 2002, provisional application No. 60/319,803, filed on Dec. 19, 2002, provisional application No. 60/481,892, filed on Jan. 14, 2004.

(51) Int. Cl.
*C02F 3/34* (2006.01)
*C12Q 1/70* (2006.01)
*C12Q 1/68* (2006.01)

(52) U.S. Cl.
USPC ............................. 435/262; 435/5; 435/6.12

(58) Field of Classification Search
None
See application file for complete search history.

(56) References Cited

U.S. PATENT DOCUMENTS

| | | | |
|---|---|---|---|
| 3,130,038 | A | 4/1964 | Thomas et al. |
| 3,378,443 | A | 4/1968 | Cooper et al. |

(Continued)

FOREIGN PATENT DOCUMENTS

| | | |
|---|---|---|
| EP | 0 763 754 A2 | 3/1997 |
| WO | WO 02/090539 A2 | 11/2002 |

(Continued)

OTHER PUBLICATIONS

Heimdahl et al., Eur. J. Clin. Microbiol. 4(4): 404-407 (1985).*

(Continued)

*Primary Examiner* — Patricia A Leith
*Assistant Examiner* — Erin M Bowers
(74) *Attorney, Agent, or Firm* — Wolf, Greenfield & Sacks, P.C.

(57) ABSTRACT

The present invention concerns compositions and methods of extracting infectious pathogens from a volume of blood. In one embodiment, the method includes the steps of creating a fibrin aggregate confining the pathogens and introducing a fibrin lysis reagent to expose the pathogens for analysis. The present invention also concerns materials and methods for removing aurintricarboxylic acid (ATA) from a sample.

13 Claims, 19 Drawing Sheets

(56) References Cited

U.S. PATENT DOCUMENTS

| | | | |
|---|---|---|---|
| 4,636,524 | A | 1/1987 | Balazs et al. |
| 4,693,972 | A | 9/1987 | Mansour et al. |
| 6,091,979 | A | 7/2000 | Madsen |
| 6,103,525 | A | 8/2000 | Stern et al. |
| 6,114,115 | A | 9/2000 | Wagner, Jr. |
| 6,261,773 | B1 | 7/2001 | Segawa et al. |
| 6,333,194 | B1 | 12/2001 | Levy et al. |
| 6,884,628 | B2 | 4/2005 | Hubbell et al. |
| 7,101,945 | B2 | 9/2006 | Dorn et al. |
| 7,118,910 | B2 | 10/2006 | Unger et al. |
| 7,135,144 | B2 | 11/2006 | Christel et al. |
| 7,211,443 | B2 | 5/2007 | Woudenberg et al. |
| 7,221,443 | B2 | 5/2007 | Akiyama |
| 7,303,876 | B2 | 12/2007 | Greenfield et al. |
| 7,306,924 | B2 | 12/2007 | Gomez et al. |
| 7,402,279 | B2 | 7/2008 | Schembri |
| 7,416,843 | B2 | 8/2008 | Ewert et al. |
| 7,476,363 | B2 | 1/2009 | Unger et al. |
| 7,687,239 | B2 | 3/2010 | Goldberg et al. |
| 7,993,870 | B2 | 8/2011 | Ewert et al. |
| 7,998,699 | B2 | 8/2011 | Ewert et al. |
| 8,465,966 | B2 | 6/2013 | Ewert et al. |
| 8,574,866 | B2 | 11/2013 | Ewert |
| 2002/0001834 | A1 | 1/2002 | Keogh et al. |
| 2002/0055109 | A1 | 5/2002 | Thill |
| 2002/0068013 | A1 | 6/2002 | Wilcox et al. |
| 2002/0111694 | A1 | 8/2002 | Ellingsen et al. |
| 2002/0128234 | A1 | 9/2002 | Hubbell et al. |
| 2002/0128310 | A1 | 9/2002 | Johansson et al. |
| 2002/0182654 | A1 | 12/2002 | Jing et al. |
| 2002/0192182 | A1 | 12/2002 | Massia et al. |
| 2005/0014128 | A1 | 1/2005 | Ewert et al. |
| 2005/0277130 | A1 | 12/2005 | Ewert et al. |
| 2009/0305383 | A1 | 12/2009 | Ewert et al. |
| 2012/0034614 | A1 | 2/2012 | Ewert et al. |
| 2012/0164714 | A1 | 6/2012 | Ewert et al. |
| 2013/0109885 | A1 | 5/2013 | Ewert |
| 2013/0115687 | A1 | 5/2013 | Ewert et al. |
| 2013/0122509 | A1 | 5/2013 | Ewert |
| 2013/0130271 | A1 | 5/2013 | Ewert |
| 2013/0130302 | A1 | 5/2013 | Ewert et al. |

FOREIGN PATENT DOCUMENTS

| | | |
|---|---|---|
| WO | 03/104251 A2 | 12/2003 |
| WO | WO 2005/021799 A2 | 3/2005 |

OTHER PUBLICATIONS

Lehman, The Enzymes 4: 251-270 (1971).*
Reddy et al., J. Biol. Chem. 247(6): 1683-1691 (1972).*
Zierdt et al., J. Clin. Microbiol. 15(1): 172-174 (1982).*
Grotendorst et al., Toxicon 37: 1779-1796 (1999).*
Gabriels, "Using a New, Fast Flow, Low Protein Binding Membrane for Sterile Filtration", 2003, http://www.millipore.com/publications.nsf/a73664f9f981af8c852569b9005b4eee/8447504c5259cf40852568f60067bd04/$FILE/PF2001EN00.pdf, accessed May 9, 2013.*
Zhang et al., J. Clin. Microbiol. 33(3): 596-601 (1995).*
Extended European Search Report for EP 09165293.3 mailed Sep. 29, 2009.
Extended European Search Report for EP 09159214.7 mailed Jul. 1, 2009.
International Preliminary Report on Patentability for PCT/US2004/026606 mailed Mar. 2, 2006.
International Search Report and Written Opinion for PCT/US2004/026606 mailed Jun. 23, 2006.
Invitation to Pay Additional Fees for PCT/US2004/026606 mailed Apr. 27, 2005.
Office Communication for Application No. AU 2004269340 mailed Apr. 22, 2009.
Office Communication for Application No. AU 2004269340 mailed Sep. 3, 2010.
Office Communication for Application No. AU 2010207760 mailed Apr. 12, 2011.
Office Communication for Application No. AU 2010207760 mailed May 24, 2012.
Office Communication for Application No. EP 04801986.3 mailed Sep. 17, 2007.
Office Communication for Application No. EP 04801986.3 mailed Nov. 13, 2006.
Office Communication for Application No. EP 09165293.3 mailed Sep. 16, 2011.
Office Communication for Application No. JP 2006-523971 mailed May 17, 2010.
Office Communication for Application No. JP 2010-108850 mailed Apr. 12, 2012.
Office Communication for U.S. Appl. No. 10/604,779 mailed Jan. 7, 2011.
Office Communication for U.S. Appl. No. 10/604,779 mailed Jan. 11, 2008.
Office Communication for U.S. Appl. No. 10/604,779 mailed Apr. 7, 2009.
Office Communication for U.S. Appl. No. 10/604,779 mailed Apr. 18, 2011.
Office Communication for U.S. Appl. No. 10/604,779 mailed Apr. 19, 2007.
Office Communication for U.S. Appl. No. 10/604,779 mailed Jun. 29, 2010.
Office Communication for U.S. Appl. No. 10/604,779 mailed Jul. 24, 2006.
Office Communication for U.S. Appl. No. 11/035,667 mailed Apr. 24, 2008.
Office Communication for U.S. Appl. No. 11/035,667 mailed Aug. 24, 2007.
Office Communication for U.S. Appl. No. 12/416,775 mailed Jan. 7, 2011.
Office Communication for U.S. Appl. No. 12/416,775 mailed Apr. 18, 2011.
Office Communication for U.S. Appl. No. 12/416,775 mailed Jun. 28, 2010.
Office Communication for U.S. Appl. No. 13/207,894 mailed Oct. 5, 2012.
Al-Soud et al., Purification and characterization of PCR-inhibitory components in blood cells. J Clin Microbiol. Feb. 2001;39(2):485-93.
Archibald et al., Comparison of BACTEC Myco/F Lytic and Wampole Isolator 10 (lysis-centrifugation) systems for detection of bacteremia, mycobacteremia, and fungemia in a developing country. J Clin Microbiol. Aug. 2000;38(8):2994-7.
Benjamin et al., *Candida rugosa* lipases: molecular biology and versatility in biotechnology. Yeast. Sep. 15, 1998;14(12):1069-87.
Bernhardt et al., Detection of bacteria in blood by centrifugation and filtration. J Clin Microbiol. Mar. 1991;29(3):422-5.
Birnboim, Rapid extraction of high molecular weight RNA from cultured cells and granulocytes for Northern analysis. Nucleic Acids Res. Feb. 25, 1988;16(4):1487-97.
Boom et al., Rapid and simple method for purification of nucleic acids. J Clin Microbiol. Mar. 1990;28(3):495-503.
Brannon et al., Clinical comparison of lysis-centrifugation and radiometric resin systems for blood culture. J Clin Microbiol. Nov. 1986;24(5):886-7.
Browne et al., Binding studies of cationic thymidyl deoxyribonucleic guanidine to RNA homopolynucleotides. Proc Natl Acad Sci USA. Jul. 18, 1995;92(15):7051-5.
Bruisten et al., Stability of HIV-1 RNA in blood during specimen handling and storage prior to amplification by NASBA-QT. J Virol Methods. Sep. 1997;67(2):199-207.
Cao et al., The purification and characterization of a phospholipase A in hamster heart cytosol for the hydrolysis of phosphatidylcholine. J Biol Chem. Dec. 15, 1987;262(35):16927-35.
Cassels et al., The interaction of streptokinase.plasminogen activator complex, tissue-type plasminogen activator, urokinase and their acylated derivatives with fibrin and cyanogen bromide digest of fibrinogen. Relationship to fibrinolytic potency in vitro. Biochem J. Oct. 15, 1987;247(2):395-400.

(56) References Cited

OTHER PUBLICATIONS

Castellino, Biochemistry of human plasminogen. Semin Thromb Hemost. Jan. 1984;10(1):18-23.

Chen et al., 1-Cys peroxiredoxin, a bifunctional enzyme with glutathione peroxidase and phospholipase A2 activities. J Biol Chem. Sep. 15, 2000;275(37):28421-7.

Cheng et al., Isolation of cultured cervical carcinoma cells mixed with peripheral blood cells on a bioelectronic chip. Anal Chem. Jun. 1, 1998;70(11):2321-6.

Cottrell, Phospholipase A2 from bee venom. Methods Enzymol. 1981;71 Pt C:698-702.

Diez et al., Isolation of full-size mRNA from cells sorted by flow cytometry. J Biochem Biophys Methods. Aug. 12, 1999;40(3):69-80.

Dupe et al., The evaluation of plasmin and streptokinase activator complexes in a new rabbit model of venous thrombosis. Thromb Haemost. Aug. 28, 1981;46(2):528-34.

Edman et al., Electric field directed nucleic acid hybridization on microchips. Nucleic Acids Res. Dec. 15, 1997;25(24):4907-14.

Ewalt et al., Detection of biological toxins on an active electronic microchip. Anal Biochem. Feb. 15, 2001;289(2):162-72.

Faux et al., Calcium chelator Quin-2 prevents crocidolite-induced DNA strand breakage in human white blood cells. Mutat Res. Dec. 1, 1994;311(2):209-15.

Fisher et al., Lysosomal-type PLA2 and turnover of alveolar DPPC. Am J Physiol Lung Cell Mol Physiol. Apr. 2001;280(4):L748-54.

Forster et al., A laminated, flex structure for electronic transport and hybridization of DNA. Biosens Bioelectron. May 2001;16(3):187-94.

Gaffney et al., Plasma fibrinogen and its fragments during streptokinase treatment. Br J Haematol. Feb. 1974;26(2):285-93.

Gamboa et al., Detection and identification of mycobacteria by amplification of RNA and DNA in pretreated blood and bone marrow aspirates by a simple lysis method. J Clin Microbiol. Aug. 1997;35(8):2124-8.

Garg et al., Simple and rapid method for extraction of DNA from fresh and cryopreserved clotted human blood. Clin Chem. Apr. 1996;42(4):647-8.

Givens et al., Inhibition of RNA-directed DNA polymerase by aurintricarboxylic acid. Nucleic Acids Res. Feb. 1976;3(2):405-18.

Gonzalez et al., Fractionation and structural elucidation of the active components of aurintricarboxylic acid, a potent inhibitor of protein nucleic acid interactions. Biochim Biophys Acta. May 24, 1979;562(3):534-45.

Gonzalez et al., Mechanism of action of polymeric aurintricarboxylic acid, a potent inhibitor of protein-nucleic acid interactions. Biochemistry. Sep. 2, 1980;19(18):4299-303.

Grotendorst et al., Purification and partial characterization of the phospholipase A2 and co-lytic factor from sea anemone (*Aiptasia pallida*) nematocyst venom. Toxicon. Dec. 1999;37(12):1779-96.

Guo et al., M(r) 6,400 aurin tricarboxylic acid directly activates platelets. Thromb Res. Jul. 1, 1993;71(1):77-88.

Hallick et al., Use of aurintricarboxylic acid as an inhibitor of nucleases during nucleic acid isolation. Nucleic Acids Res. Sep. 1977;4(9):3055-64.

Hamilton et al., Effect of delay in processing on lysis-centrifugation blood culture results from marrow transplant patients. J Clin Microbiol. Jul. 1989;27(7):1588-93.

Heininger et al., The effect of human serum DNAases on the ability to detect antibiotic-killed *Escherichia coli* in blood by PCR. J Med Microbiol. Mar. 2001;50(3):243-8.

Hoffman et al., Bone marrow aspirate culture superior to streptokinase clot culture and 8 ml 1:10 blood-to-broth ratio blood culture for diagnosis of typhoid fever. Am J Trop Med Hyg. Jul. 1986;35(4):836-9.

Huang et al., Electric manipulation of bioparticles and macromolecules on microfabricated electrodes. Anal Chem. Apr. 1, 2001;73(7):1549-59.

Kiss et al., Improved subtractive suppression hybridization combined with high density cDNA array screening identifies differentially expressed viral and cellular genes. J Virol Methods. Feb. 2003;107(2):195-203.

Kreilgaard et al., Effects of additives on the stability of recombinant human factor XIII during freeze-drying and storage in the dried solid. Arch Biochem Biophys. Dec. 1, 1998;360(1):121-34.

Leal-Klevezas et al., Single-step PCR for detection of *Brucella* spp. from blood and milk of infected animals. J Clin Microbiol. Dec. 1995;33(12):3087-90.

Lee et al., Direct identification of *Vibrio vulnificus* in clinical specimens by nested PCR. J Clin Microbiol. Oct. 1998;36(10):2887-92.

Li et al., Effects of volume and periodicity on blood cultures. J Clin Microbiol. Nov. 1994;32(11):2829-31.

Li et al., Transport, manipulation, and reaction of biological cells on-chip using electrokinetic effects. Anal Chem. Apr. 15, 1997;69(8):1564-8.

Lonneborg et al., Reliable and reproducible method to extract high-quality RNA from plant tissues rich in secondary metabolites. Biotechniques. Oct. 2000;29(4):714, 716-8.

Malin et al., Effect of tetrahydropyrimidine derivatives on protein-nucleic acids interaction. Type II restriction endonucleases as a model system. J Biol Chem. Mar. 12, 1999;274(11):6920-9.

Malin et al., Induction of synthesis of tetrahydropyrimidine derivatives in *Streptomyces* strains and their effect on *Escherichia coli* in response to osmotic and heat stress. J Bacteriol. Jan. 1996;178(2):385-95.

Menashe et al., Hydrolysis of dipalmitoylphosphatidylcholine small unilamellar vesicles by porcine pancreatic phospholipase A2. J Biol Chem. Apr. 25, 1986;261(12):5328-33.

Miles et al., Binding and activation of plasminogen on the platelet surface. J Biol Chem. Apr. 10, 1985;260(7):4303-11.

Molloy et al., Proteomic analysis of the *Escherichia coli* outer membrane. Eur J Biochem. May 2000;267(10):2871-81.

Morata et al., Diagnostic yield of a PCR assay in focal complications of brucellosis. J Clin Microbiol. Oct. 2001;39(10):3743-6.

Morata et al., Posttreatment follow-Up of brucellosis by PCR assay. J Clin Microbiol. Dec. 1999;37(12):4163-6.

Nadano et al., Measurement of deoxyribonuclease I activity in human tissues and body fluids by a single radial enzyme-diffusion method. Clin Chem. Mar. 1993;39(3):448-52.

Nakane et al., Differential inhibition of various deoxyribonucleic acid polymerases by Evans blue and aurintricarboxylic acid. Eur J Biochem. Oct. 15, 1988;177(1):91-6.

Nguyen et al., Thrombolysis using liposomal-encapsulated streptokinase: an in vitro study. Proc Soc Exp Biol Med. Dec. 1989;192(3):261-9.

Oberbaumer et al., Detection of RNA on northern blots by negative staining with aurintricarboxylic acid. Anal Biochem. Feb. 15, 1990;185(1):77-9.

Oikawa et al., Site-specific DNA damage at GGG sequence by oxidative stress may accelerate telomere shortening. FEBS Lett. Jun. 25, 1999;453(3):365-8.

Park et al., Photopolymerized hyaluronic acid-based hydrogels and interpenetrating networks. Biomaterials. Mar. 2003;24(6):893-900.

Pierre et al., Purification and characterization of the cytochrome b6 f complex from *Chlamydomonas reinhardtii*. J Biol Chem. Dec. 8, 1995;270(49):29342-9.

Polymerase Chain Reaction for Rapid Diagnosis of Candidemia. Bull Acad Mil Med Science. 1998;22(3).

Qiagen Qiamp DNA Mini Kit and QIAamp DNA Blood Mini Kit Handbook. Quigen. Feb. 2003:1-66.

Queipo-Ortuno et al., Rapid diagnosis of human brucellosis by peripheral-blood PCR assay. J Clin Microbiol. Nov. 1997;35(11):2927-30.

Read, Recovery efficiencies on nucleic acid extraction kits as measured by quantitative LightCycler PCR. Mol Pathol. Apr. 2001;54(2):86-90.

Rozalski et al., Effects of fibrinogen receptor antagonist GR144053F and aurintricarboxylic acid on platelet activation and degranulation. Biochem Pharmacol. Nov. 15, 2001;62(10):1399-408.

(56) References Cited

OTHER PUBLICATIONS

Sanyal et al., An effective method of completely removing contaminating genomic DNA from an RNA sample to be used for PCR. Mol Biotechnol. Oct. 1997;8(2):135-7.
Semple et al., Novel, potent and selective chimeric FXa inhibitors featuring hydrophobic P1-ketoamide moieties. Bioorg Med Chem Lett. Oct. 16, 2000;10(20):2305-9.
Shipolini et al., Phospholipase A from bee venom. Eur J Biochem. Jun. 29, 1971;20(4):459-68.
Siersema et al., Blood culture bottles are superior to lysis-centrifugation tubes for bacteriological diagnosis of spontaneous bacterial peritonitis. J Clin Microbiol. Mar. 1992;30(3):667-9.
Skidmore et al., Characterization and use of the potent ribonuclease inhibitor aurintricarboxylic acid for the isolation of RNA from animal tissues. Biochem J. Oct. 1, 1989;263(1):73-80.
Smith et al., Acyl-enzymes as thrombolytic agents in a rabbit model of venous thrombosis. Thromb Haemost. Jun. 28, 1982;47(3):269-74.
Snitko et al., High specificity of human secretory class II phospholipase A2 for phosphatidic acid. Biochem J. Feb. 1, 1997;321 ( Pt 3):737-41.
Sponer et al., Electronic properties, hydrogen bonding, stacking, and cation binding of DNA and RNA bases. Biopolymers. 2001-2002;61(1):3-31.
Titball, Bacterial phospholipases C. Microbiol Rev. Jun. 1993;57(2):347-66.
Tsutsui et al., Fractionation of aurintricarboxylic acid and effects of its components on nuclear swelling and nucleic acid synthesis. Biochim Biophys Acta. Jan. 26, 1978;517(1):14-23.
Von Pape et al., Platelet function analysis with PFA-100 in patients medicated with acetylsalicylic acid strongly depends on concentration of sodium citrate used for anticoagulation of blood sample. Thromb Res. May 15, 2000;98(4):295-9.
Wang et al., Polymyxin B binds to anandamide and inhibits its cytotoxic effect. FEBS Lett. Mar. 24, 2000;470(2):151-5.
Wang et al., Simultaneous measurement of anandamide and 2-arachidonoylglycerol by polymyxin B-selective adsorption and subsequent high-performance liquid chromatography analysis: increase in endogenous cannabinoids in the sera of patients with endotoxic shock. Anal Biochem. Jul. 1, 2001;294(1):73-82.
Watson, Laboratory and clinical investigation of recovery of *Salmonella typhi* from blood. J Clin Microbiol. Feb. 1978;7(2):122-6.
Yang et al., An integrated, stacked microlaboratory for biological agent detection with DNA and immunoassays. Biosens Bioelectron. Jun. 2002;17(6-7):605-18.
Zhang et al., Detection of *Streptococcus pneumoniae* in whole blood by PCR. J Clin Microbiol. Mar. 1995;33(3):596-601.
Zhang et al., Effect of six steroidal saponins isolated from anemarrhenae rhizoma on platelet aggregation and hemolysis in human blood. Clin Chim Acta. Nov. 1999;289(1-2):79-88.
Zierdt et al., Development of a lysis-filtration blood culture technique. J Clin Microbiol. Jan. 1977;5(1):46-50.
Zierdt, Blood-lysing solution nontoxic to pathogenic bacteria. J Clin Microbiol. Jan. 1982;15(1):172-4.
Office Communication for Application No. EP 09165293.3 dated Jan. 23, 2013.
Notice of Allowance for U.S. Appl. No. 12/117,505 dated Feb. 22, 2013.
Office Communication for U.S. Appl. No. 13/725,113 dated Mar. 1, 2013.
Office Communication for U.S. Appl. No. 13/725,568 dated Apr. 23, 2013.
Office Communication for U.S. Appl. No. 13/725,924 dated Apr. 25, 2013.
Office Communication for U.S. Appl. No. 13/725,495 dated Apr. 1, 2013.
Office Communication for U.S. Appl. No. 13/725,435 dated Apr. 8, 2013.
[No Author Listed] Novagen, MagPrep Streptavidin Beads. Available at http://www.ebiotrade.com/buyf/productsf/Novagen/70716-000.pdf, published Nov. 1999, accessed Mar. 21, 2013. 4 pages.
Evans et al., Ionic Transport in the Fish Gill Epithelium. J Exp Zool. 1999;283:641-52.
Reznik et al., Streptavidins with intersubunit crosslinks have enhanced stability. Nat Biotechnol. Aug. 1996;14(8):1007-11.
Schryvers et al., Identification and characterization of the human lactoferrin-binding protein from *Neisseria meningitidis*. Infect Immun. May 1988;56(5):1144-9.
Tillett et al., The Effect in Patients of Streptococcal Fibrinolysin (Streptokinase) and Streptococcal Desoxyribonuclease on Fibrinous, Purulent, and Sanguinous Pleural Exudations. J Clin Invest. Jan. 1949;28(1):173-90.
Weber et al., Structural origins of high-affinity biotin binding to streptavidin. Science. Jan. 6, 1989;243(4887):85-8.
Office Communication for Application No. AU 2012216623 dated Aug. 1, 2013.
Notice of Acceptance for Application No. AU 2012216623 dated Sep. 11, 2013.
Office Communication for U.S. Appl. No. 13/725,944 dated Sep. 6, 2013.
Notice of Allowance for U.S. Appl. No. 13/725,303 mailed Jun. 28, 2013.
Notice of Allowance for U.S. Appl. No. 13/725,196 mailed Jul. 23, 2013.
Office Communication for U.S. Appl. No. 13/725,113 dated Aug. 29, 2013.
Office Communication for U.S. Appl. No. 13/725,568 dated Oct. 21, 2013.
Office Communication for U.S. Appl. No. 13/725,924 mailed Oct. 10, 2013.
Office Communication for U.S. Appl. No. 13/725,495 mailed Oct. 9, 2013.
Office Communication for U.S. Appl. No. 13/725,435 mailed Oct. 9, 2013.
Office Communication for U.S. Appl. No. 13/852,938 dated Jul. 8, 2013.
Cliffton et al., Fibrinolytic and proteolytic activity of a human plasminogen, prepared from fraction III of human plasma. J Appl Physiol. Jul. 1953;6(1):42-50.
Leach et al., Photocrosslinked hyaluronic acid hydrogels: natural, biodegradable tissue engineering scaffolds. Biotechnol Bioeng. Jun. 5, 2003;82(5):578-89.
Office Communication dated May 8, 2013 for U.S. Appl. No. 13/725,651.
Lucore et al., Immobilization with metal hydroxides as a means to concentrate food-borne bacteria for detection by cultural and molecular methods. Appl Environ Microbiol. May 2000;66(5):1769-76.
Notice of Allowance for U.S. Appl. No. 13/725,944 mailed Oct. 30, 2013.
Office Communication for U.S. Appl. No. 13/725,651 mailed Nov. 15, 2013.
Sullivan et al., Practical aerobic membrane filtration blood culture technique: development of procedure. J Clin Microbiol. 1975;1(1):30-6.
Office Communication for U.S. Appl. No. US 13/725,113 mailed Apr. 17, 2014.
Notice of Allowance for U.S. Appl. No. US 13/725,924 mailed Apr. 16, 2014.
Office Communication for U.S. Appl. No. US 13/725,495 mailed Mar. 11, 2014.
Office Communication for U.S. Appl. No. US 13/725,651 mailed Feb. 28, 2014.

\* cited by examiner

FIG. 13

Noise band crossing points for blood samples spiked with *B. anthracis* and processed with plasminogen, streptokinase, phospholipase A$_2$, DNase I, and lipase with centrifugation or filtration

| Amount *B. anthracis* Seeded (cfu) | Centrifugation Noise Band Crossing Points | | | Mean | Std. Dev. | Filtration Noise Band Crossing Points | | | Mean | Std. Dev. |
|---|---|---|---|---|---|---|---|---|---|---|
| ≤ 0.01 | | | | | | | | | | |
| ≤ 0.01 | | | | | | | | | | |
| ≤ 1.0 | | | | | | 40.33 | 39.89 | | 40.11 | |
| ≤ 1.0 | | | | | | | 37.79 | | 37.79 | |
| ≤ 2.0 | | | | | | 40.36 | | 37.69 | 39.03 | |
| ≤ 2.0 | 41.93 | | 40.31 | 41.12 | | | | | | |
| ≤ 5.0 | | | 40.47 | 40.47 | | 37.90 | 37.70 | 37.79 | 37.80 | 0.10 |
| ≤ 5.0 | 38.11 | | 40.36 | 39.24 | | 36.45 | 36.09 | 36.81 | 36.45 | 0.36 |
| ≤ 50.0 | 37.53 | 36.24 | 37.90 | 37.22 | 0.87 | 35.75 | 34.12 | 34.98 | 34.95 | 0.82 |
| ≤ 50.0 | 36.45 | 38.15 | 38.49 | 37.70 | 1.09 | 35.24 | 34.18 | 34.68 | 34.70 | 0.53 |

FIG. 14

Sedimentation and solublization of tissue aggregates from 6 ml blood samples exposed to various detergent and enzyme treatments

Enzyme treatments in a PBS/Triton X-100 buffer

|  | Triton X-100 in PBS | Pl.[c] 1U | Ph.[b] | Pl.[c] 1U Ph.[b] | Dn.[a] 1mg | Dn.[a] 1 mg Ph.[b] | Dn.[a] 1 mg Pl.[c] 1U Ph.[b] |
|---|---|---|---|---|---|---|---|
| % Observable pelleted tissue aggregate post centrifugation | 100 | 100 | 100 | 100 | 90 | 10 | 10 |
| Time (min) to solubilization of visible tissue aggregate in BLB[d] | > 360 | > 60 | > 60 | > 60 | < 10 | < 0.5 | < 0.5 |

[a] DNase I from the Roche MagNa Pure LC DNA Kit III
[b] Phospholipase $A_2$
[c] Plasminogen and 10K U streptokinase
[d] Bacterial Lysis Buffer from the Roche MagNa Pure LC DNA Kit III

FIG. 15

Filtration characteristics of 6 ml blood samples exposed to various detergent and enzyme treatments

| | Triton X-100 in PBS | Dn.[a] 1mg | Dn.[a] 1 mg Ph.[b] | Pl.[c] 5U | Pl.[c] 5U Dn.[a] 1mg Ph.[b] | Pl.[c] 5U Dn.[a] 0.2mg Ph.[b] | Pl.[c] 10U Dn.[a] 0.2mg Ph.[b] |
|---|---|---|---|---|---|---|---|
| Not filterable | + | + | + | | | | |
| Filterable with observable tissue aggregates | | | | + | | + | |
| Filterable with out observable aggregates | | | | | + | | + |

[a] DNase I from the Roche MagNa Pure LC DNA Kit III
[b] Phospholipase A$_2$
[c] Plasminogen converted to plasmin with 10K U streptokinase

US 8,785,176 B2

POST PROTEIN HYDROLYSIS REMOVAL OF A POTENT RIBONUCLEASE INHIBITOR AND THE ENZYMATIC CAPTURE OF DNA

CROSS-REFERENCE TO RELATED APPLICATIONS

This application is a continuation of U.S. application Ser. No. 13/725,924 filed Dec. 21, 2012; which is a continuation of U.S. application Ser. No. 12/117,505, filed May 8, 2008; which is a divisional application of U.S. application Ser. No. 11/035,667, filed Jan. 14, 2005; U.S. application Ser. No. 11/035,667 is a continuation-in-part of U.S. application Ser. No. 10/604,779, filed Aug. 15, 2003; U.S. application Ser. No. 10/604,779 claims the benefit of U.S. Provisional application Ser. No. 60/319,474, filed Aug. 15, 2002, and U.S. Provisional application Ser. No. 60/319,803, filed Dec. 19, 2002; U.S. application Ser. No. 11/035,667 claims the benefit of U.S. Provisional application Ser. No. 60/481,892, filed Jan. 14, 2004; U.S. application Ser. No. 11/035,667 is a continuation-in-part of International application No. PCT/US2004/026606, filed Aug. 16, 2004; which claims priority to U.S. application Ser. No. 10/604,779, filed Aug. 15, 2003, and claims the benefit of U.S. Provisional application Ser. No. 60/481,892, filed Jan. 14, 2004; the disclosure of all of which is incorporated herein by reference in its entirety.

This invention was made with government support under Grant No. DAAD13-01-C-0043 awarded by the U.S. Army Soldier and Biological Chemical Command. The government has certain rights in the invention.

BACKGROUND OF THE INVENTION

The threat of bioterrorism (BT) and biological warfare presents challenges for the clinical setting that are best met with rapid and sensitive technologies to detect BT agents. Peripheral blood samples could contribute to early and specific clinical and epidemiological management of a biological attack if detection could take place when the concentration of the infecting organism is still very low. The worried well and recently infected patients would benefit, both psychologically and physically, from early pharmacological intervention.

Infection with *Bacillus anthracis* or *Yersinia pestis* often present initially as a nonspecific febrile or flu-like illness. The mediastinitis associated with inhalational anthrax ultimately results in bacilli entering the blood once the efferent lymphatics become laden with organisms. When bacteremia (the presence of bacteria in the blood) and sepsis (the invasion of bodily tissue by pathogenic bacteria) have initiated, the number of bacilli may increase quickly, doubling every 48 minutes, most often resulting in death of the patient.

It has been reported that microbiological studies on patient blood samples are useful for diagnosing pneumonic plague. The potential for *Yersinia pestis* bacilli to be present in peripheral circulating blood suggests that a PCR assay would make a useful diagnostic tool. Testing for pneumonic plague or inhalational anthrax would be effective when healthy patients present with "flu-like" symptoms (malaise, fever, cough, chest pain and shortness of breath) that may accompany other nonspecific symptoms. However, in order to maximize the probability of successful treatment, detection of the infecting organism must take place early in the disease process, when the concentration of circulating bacteria is very low.

Extraction of pathogen DNA from whole blood typically requires between 200 µl to 500 µl of whole peripheral blood patient sample for each preparation event. Detection of early bacteremia is improved by using an entire 6 to 10 ml tube of patient blood for a single sample preparation event. Prior art literature describes a single tube blood culture system exploiting the selective lysis of blood elements, followed by centrifugation to pellet bacteria for plating on solid media. The technique has been examined thoroughly in conjunction with microbiological testing. Previous methods based on lyses of blood cells followed by centrifugation have not proven to be useful for nucleic acid or biosensor based detection protocols.

Accordingly, what is needed in the art is: 1) a method of destroying and making soluble the spectrum of blood element components (erythrocytes, leukocytes, nuclear membranes, fibrin, and host nucleic acid) without damaging analyte particles (bacteria, virus, fungi, toxin, metabolic markers, disease state markers, or chemical agents) in order to expose and rapidly concentrate (via centrifugation, filtration, or capture) the analyte particles from large volumes of blood, 2) processing to minimize inhibition and/or removal of the host DNA and the matrix associated biomass present in the large volume blood sample using a single step enzyme detergent cocktail that is amenable to automation and portable systems, and 3) an analyte particle concentration method that can be coupled to existing manual or automated processes for nucleic acid extraction, biosensor testing, or liquid chromatography separation and mass spectrometry analysis. It is, therefore, to the effective resolution of the aforementioned problems and shortcomings of the prior art that the present invention is directed.

Fibrin is an insoluble protein precipitated from blood that forms a network of fibers. In vivo, this process is central to blood clotting. Fibrin is created by the proteolytic cleavage of terminal peptides in fibrinogen. In the laboratory analysis of blood, an aggregate (pellet) of fibrin combined with other blood elements sediments at the bottom of a tube when blood is centrifuged. Within the fibrin aggregate, pathogens are trapped. The analysis of these pathogens is highly desirable. However, like coins embedded in a slab of concrete, the captured pathogens are substantially hidden from analysis, trapped in the fibrin aggregate. For individuals potentially exposed to dangerous pathogens, time is of the essence and rapid identification of the captured pathogens is paramount. Rapid identification of nucleic acid, proteins, or other molecules associated with bacteria, virus, fungi, toxin, metabolic markers, disease state markers, or chemical agents is important for individual clinical management as well as forensic and epidemiological investigation.

Plasmin is a substance in blood capable of converting fibrin to fibrinogen monomers. Plasminogen is a precursor of plasmin in the blood. Streptokinase is an enzyme that activates plasminogen to form plasmin. The combination of plasminogen and streptokinase in the presence of the fibrin aggregate containing blood elements and bacteria (formally present in peripheral circulation) allows the conversion of the fibrin aggregate to a liquid state. Plasminogen activators are naturally occurring enzymes found in most all vertebrate species. These enzymes in any combination can also be used to derive beneficial blood matrix disassembly where the downstream application require clots or blood element aggregates to be dissolved in order to facilitate sample flow and analyte interrogation.

Aurintricarboxylic acid (ATA) is a polymeric anion that has been demonstrated in the literature to be a potent ribonuclease inhibitor. The compound has been described previously as an additive to sample lysis buffers where the objective is to extract RNA species from tissue samples. The nucleic acid extract derived from such procedures has been shown to be suitable for hybridization and gel electrophoresis analysis. However, ATA is a potent inhibitor of reverse transcriptase, which is essential for the polymerase chain reaction (PCR) detection of RNA species. Published procedures to remove ATA from nucleic acid containing compositions have revolved around chromatographic procedures that eliminate or remove only a portion of the ATA.

The use of ATA in a proteinase K lysis buffer is potentially superior to 1) chaotrophic salts (since they tend to reduce the efficiency of proteinase K driven protein hydrolysis as evidenced by PCR results); 2) protein based ribonuclease inhibitors (since these inhibitors would be broken down by proteinase K); and 3) EDTA (which only indirectly inhibits nucleases via chelation of the divalent cations used by those nucleases). In fact, divalent cations must be added to RNA preparations where enzymatic DNA hydrolysis is conducted. What has not been demonstrated in prior art is a method where, once added, the complete downstream removal of ATA from nucleic acid extracts can be achieved to the point that downstream reverse transcriptase PCR (RT-PCR) will function. Also not previously described is a way to utilize ATA in a lyses buffer to treat a large volume (1 to 10 ml) of whole blood sample and after several reagents addition steps move directly to RNA array hybridization using the entire blood sample for one analysis event hence bypassing RNA extraction and amplification.

Also not previously described is a way to selectively allow non-diagnostic RNA species residing outside the nucleus of leukocytes to be degraded by endogenous and or exogenous nucleases while diagnostic RNA which mostly resides inside the nucleus (RNA that for instance indicates up or down regulation of genes) is preserved enough for array or amplification based detection. Typically, chemistries that do not provide abundant intact ribosomal RNA are not further examined because end users skilled in the art use such non diagnostic RNA species to judge overall RNA integrity. Based on biochemical and phenotypical differences between phospholipid membranes found in various blood elements and the combined biochemical activity characteristics of the reagent cocktail, RNA species such as globin and ribosomal RNA are destroyed but the diagnostic mRNA which is used to detect presence or absence of various disease and or pathological processes is preserved enough for identification. Also, by allowing for the bulk of non-diagnostic RNA to be destroyed, there is less inhibition of PCR (polymerase chain reaction) contributed by the nucleic acid extract.

ATA also serves an important function in the protection of bacterial DNA when that bacteria is present in a blood sample processed with reagents containing high levels ($\geq 100$ U/ml) of DNase I as is used in various embodiments contained within U.S. application Ser. No. 10/604,779. In order to achieve RNA detection capabilities that are superior to what can be achieved with technology descried in U.S. application Ser. No. 10/604,779, and to do so without additional steps or requirements, the present invention is utilized in combination with blood sample treatment technology described in U.S. application Ser. No. 10/604,779 and prior art nucleic acid extraction methods that utilize chaotrophic salts such as guanidine thiocyanate in the presence of capture matrices such as silica or methods that utilize precipitation methods to concentrate nucleic acids out of crude samples.

BRIEF SUMMARY OF THE INVENTION

The present invention concerns compositions and methods of extracting and detecting infectious pathogens from a volume of blood. In one embodiment, the method includes the steps of creating a fibrin aggregate confining the pathogens; introducing an enzyme based Blood Processing Reagent to expose the pathogens for analysis and to facilitate pathogen DNA extraction. In one embodiment, the enzyme based Blood Processing Reagent may be composed of DNAse, plasminogen and streptokinase frozen in coincident relation until the fibrin lysis reagent is needed whereby streptokinase enzymatically reacts with plasminogen to form plasmin upon thawing and introduction into the fibrin aggregate sample. The DNAse enzyme is used to facilitate the chemical and physical disruption of pelleted blood elements that result from the previously described protocol in addition to other benefits described herein. Preferably, the plasminogen is suspended in an aqueous salt solution, including NaCl and $Na_3PO_4$, prior to freezing. The fibrin lysis reagent can also comprise Phospholipase $A_2$. Phospholipase $A_2$ is used to help non-pathogen DNA digestion by destroying phospholipid bilayers and, hence, destruction of the nuclear membrane.

The subject invention also concerns materials and methods for efficiently removing ATA from a nucleic acid composition. The subject methods provide a nucleic acid composition sufficiently free of ATA such that a RT-PCR reaction and other reactions involving reverse transcriptase can be performed.

The subject invention also concerns materials and methods for a mixture of ATA, magnesium chloride, potassium phosphate, and sodium chloride that is dried and combined with other dried components such as those described herein.

The subject invention also concerns materials and methods for heating a solution of urea, DTPA, optionally containing EDTA, sodium citrate, and sodium chloride, to between about 400 to 600° C. for 1 to 4 hours followed by drying and combination with proteinase K and optionally Methyl 6-O-(N-heptylcarbamoyl)-α-D-glucopyranoside and the use of this sample Lyses Reagent to allow ATA removal from nucleic acid extracts made with existing prior art methods based on chaotrophic salts or nucleic acid precipitation followed by centrifugation or methods descried herein to allow downstream hybridization of RNA species directly out of treated whole blood samples.

The subject invention also concerns the urea/DTPA sample Lyses Reagent that was heat treated to 400 to 600° C. for 1 to 4 hours during production and used in sample treatment as descried above followed by the combination of urease to break down the urea followed by RNA array analysis.

The subject invention also concerns materials and methods for pathogen capture using bioactive peptides functionalized on hyaluronic acid as described herein where the hyaluronic acid in turn acts as a polymeric waveguide.

The subject invention also concerns a way to cause a calcium release at the site of pathogen capture via bioactive peptide or annealing of RNA species so as to trigger the conversion of reporter molecule labeled fibrinogen to insoluble fibrin at the site of pathogen capture via bioactive peptide or annealing of RNA species upon the matrix of the hyaluronic acid polymeric waveguide.

The subject invention also concerns materials and methods where the hyaluronic acid matrix that is cross linked utilizing biotin and strepavidin and functionalized with bioactive peptides, such as those described herein, can be subsequently broken down with hyaluronidase in order to facilitate pathogen elution.

The subject invention is practiced in conjunction with methods and materials for extracting infectious pathogens from a volume of a sample, such as blood, including the steps of creating a fibrin aggregate confining the pathogens and introducing an enzyme based Blood Processing Reagent to expose the pathogens for analysis and DNAse to facilitate DNA extraction specified in U.S. application Ser. No. 10/604,779, filed Aug. 15, 2003. The enzyme based Blood Processing Reagent may be composed of DNAse, plasminogen and streptokinase frozen in coincident relation until the fibrin lysis reagent is needed whereby streptokinase enzymatically reacts with plasminogen to form plasmin upon thawing and introduction into the fibrin sample. Preferably, the plasminogen is suspended in an aqueous salt solution prior to freezing including NaCl and $Na_3PO_4$. The enzyme based Blood Processing Reagent is preferably composed of DNAse and Phospholipase $A_2$. The DNAse enzyme is used to facilitate the chemical and physical disruption of pelleted blood elements that result from the previously described protocol. Phospholipase $A_2$ is used to help human DNA digestion by destroying phospholipid bilayers and, hence, destruction of the nuclear membrane.

The subject invention also pertains to materials and methods for efficiently removing human DNA that has been processed or cleaved by DNAse, endonuclease, or exonuclease while pathogen DNA remains inside intact pathogens. Single Strand Binding (SSB) proteins are known in the art to enhance PCR kinetics through binding to DNA and can also be used in the methods of the invention. In an exemplified embodiment, the SSB is biotinylated and the solid matrix has avidin or streptavidin attached to the surface, and the SSB is bound to the matrix via the biotin-avidin binding. In one embodiment of the method, a purified nucleic acid extract sample is optionally combined with proline at 2 to 20 mM and or DTT at 2 to 5 mM then circulated for several minutes at about 37° C. with the immobilized SSB. The SSB-matrix and bound human DNA is separated from the sample and the remaining sample collected. The remaining sample contains nucleic acid with a reduced human DNA load and can be used for PCR testing. Since DNAse, endonuclease, or exonuclease will nick human DNA in the presence of ATA and or other nuclease inhibitors described herein combined with the other biochemical elements described in U.S. application Ser. No. 10/604,779, while pathogen DNA residing inside intact pathogen structures is not nicked, a portion of the inhibitory human DNA can be selectively removed in this way post nucleic acid extraction.

The subject invention also pertains to the use of nuclease inhibitors with or without ATA plus high levels of DNAse, endonuclease, or exonuclease (over 200 U/ml). The combination of nuclease inhibitors and nucleases teaches against the art but leads to processing of human DNA so that said DNA presents a small inhibitory contribution to PCR reactions compared to the same amount of human DNA that is not contacted with this reagent mixture.

In applications when RNA purification is desired, solutions used in the subject methods should be RNase-free. RNase-free solutions can be prepared using methods known in the art, including treatment with DEPC, typically at about 0.1%. DEPC treated water should be used to wash and rinse any glass or plasticware used in RNA isolation methods that is not RNase-free. Residual DEPC should always be eliminated from solutions or glassware/plasticware by autoclaving or heating to 100° C. for 15 minutes.

BRIEF DESCRIPTION OF THE DRAWINGS

FIG. 13 is a table providing data on noise band crossing points for blood samples spiked with *B. anthracis* and processed with plasminogen, streptokinase, phospholipase $A_2$, DNase I, and lipase with centrifugation or filtration.

FIG. 14 shows sedimentation and solubilization of tissue aggregates from 6 ml blood samples exposed to various detergent and enzyme treatments.

FIG. 15 shows filtration characteristics of 6 ml blood samples exposed to various detergent and enzyme treatments.

FIG. 16 shows the results pathogen detection by canonical SNP analysis using the present invention.

FIG. 17 is a bar chart showing detection of CRP in whole blood treated in a Blood Processing reagent of the present invention.

DETAILED DISCLOSURE OF THE INVENTION

The present invention concerns compositions and methods of extracting and detecting infectious pathogens, components thereof, or other matter, such as prions, toxins, metabolic markers, cancerous matter or markers, disease state markers, and the like, from a volume of blood or other biological sample from a patient, such as a human or other mammal. In one embodiment, the method comprises preparing a fibrin aggregate of a blood sample to confine pathogens; contacting the fibrin aggregate with a fibrin lyses reagent to release pathogens or pathogen components trapped in the aggregate; lysing pathogens and/or extracting pathogen nucleic acids or other pathogen components; and detecting the pathogens, nucleic acids and/or components. Pathogen analysis can be accomplished by any appropriate means including, but not limited to, blood culture, antibody based testing, or nucleic acid sequence based testing (PCR, Reverse Transcription PCR, NASBA, TMA or the like).

In one embodiment, the fibrin lysis reagent may be composed of a nuclease, plasminogen and streptokinase frozen in coincident relation until the fibrin lysis reagent is needed. Upon thawing and introduction into the fibrin aggregate sample, streptokinase enzymatically reacts with plasminogen to form plasmin. The nuclease enzyme facilitates the chemical and physical disruption of pelleted blood elements. Nucleases contemplated within the scope of the present invention include, but are not limited to, DNAses, endonucleases, and exonucleases. Preferably, the plasminogen is suspended in an aqueous salt solution, including NaCl and $Na_3PO_4$, prior to freezing. The fibrin lysis reagent can also comprise Phospholipase $A_2$. Phospholipase $A_2$ is useful to help non-pathogen DNA digestion by destroying phospholipid bilayers and, hence, destruction of the nuclear membrane.

In another embodiment, the enzymes of the fibrin lysis reagent can be provided in a dried form and then when ready to be used in the present methods resuspended in a buffer solution using Potassium Phosphate as an aide to blood element solubilization. It is imperative that the streptokinase and plasminogen are not mixed with the buffer solution until immediately prior to addition to the blood sample. The Potassium Phosphate pH range can be about 7.8 to about 8.0, differentiated from prior art claiming an effective pH range of 7.2 to 7.6. The prior art teaches the use of phosphate ion solutions with lower pH to act as a true buffer; however, the method of the present invention allows for optimal Phospholipase $A_2$ activity and Magnesium solubility. The Potassium Phosphate acts as an essential component for blood matrix disassembly when any of the enzyme combinations described herein are used. This contribution to blood matrix disassembly is comprised of biochemical interactions that are unrelated to buffering of pH. This contribution of Potassium Phosphate to enzymatic driven blood matrix disassembly has never been described before. When Potassium Phosphate is omitted and replaced with another buffer such as Tris-HCL, blood element disassembly does not occur and the blood sample matrix remains incompatible for analysis. Magnesium can be present in the buffer solution as a divalent cation driving the activity of Phospholipase $A_2$ in the presence of DNase. Prior art uses calcium as the classic divalent cation for driving Phospholipase $A_2$ activity; however, calcium is not compatible with the phosphate ions essential for blood element solublization.

Figure 1:
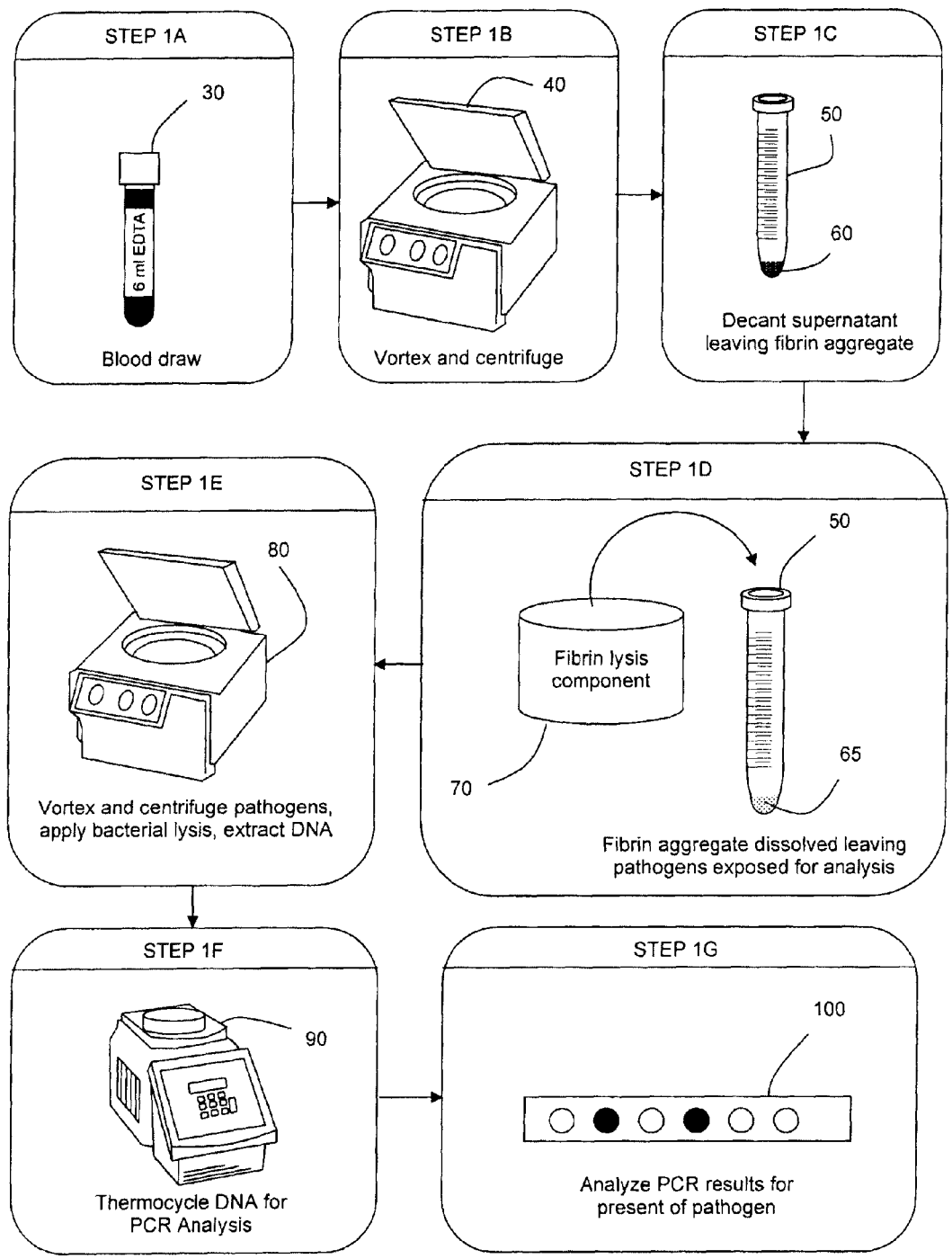
FIG. 1 is a diagrammatic view of the method according to the invention according to the invention.

Enzymes that may be used in addition to or in place of plasminogen and/or streptokinase fall into five categories: 1) mutants or variants of single chain urokinase type plasminogen activator; 2) mutants or variants of tissue type plasminogen activator; 3) recombinant chimaeric plasminogen activators; 4) conjugates of plasminogen activators and anti-fibrin monoclonal antibodies; and 5) compounds derived from haemophagous animals (including salivary plasminogen activator from vampire bats), venom from southern copperhead snakes, antithrombolytic enzymes derived from leeches such as *Hirudo medicincalis, Hirdinaria manillensis* or *Haementeria ghillanii*, and staphylokinase from bacteria.

By including DNAse in the enzyme based Blood Processing Reagent, sample processing is facilitated by the conversion of DNA of the patient's blood cells into short fragments thereby contributing to a more rapid and efficient protein hydrolysis process during DNA extraction and lowering the burden of inhibitory DNA. Similarly, introduction of an endonuclease or an exonuclease produces a similar advantage. The addition of DNAse (a DNA nuclease), endonuclease, and/or exonuclease in the methods of the invention provides for the conversion of DNA into short fragments. This conversion of DNA into short fragments contributes to a more rapid and efficient protein hydrolysis process during DNA extraction. This conversion of the patient's blood DNA into short fragments is done while the bacterial DNA is protected. The short fragment DNA is carried less efficiently through the DNA extraction process and hence represents a smaller proportion of total DNA product. As a result, the reduced patient DNA level presents less of an inhibitory component to the nucleic acid sequence based reactions. What human DNA that does carry over into the sample extract is processed by DNAse, endonuclease, and/or exonuclease, preferably in the presence of aurintricarboxylic acid. Other nuclease inhibitors that can be used include salts of ATA, e.g., ATA triammonium salt, Ethylene glycol-bis(2-aminoethylether)-N,N,N,N-tetraacetic acid, Netropsin dihydrochloride, or 1,10-Phenanthroline monohydrate, formaurin-dicarboxylic acid, Evans Blue (a structural analogue of suramin), vanadyl ribonucleoside complexes, nuclease inhibitors based on poly vinylsulfonate, and the nuclease inhibition enhancer $ZnCl_2$ in such a way that the human does not inhibit downstream nucleic acid based detection systems.

The use of nuclease inhibitors such as these, in reactions intended to hydrolyze DNA with nucleases, teaches against the art. The outcome is preservation of pathogen DNA contained within intact pathogens while patient DNA is processed to facilitate proteinase K digestion plus overall breakdown of the blood sample components when other reagents specified herein are used and also to process the patient DNA so that it will not inhibit downstream nucleic acid detection reactions.

The enzyme based Blood Processing Reagent comprising plasminogen may further comprise Phospholipase $A_2$, DNase, Endonuclease, Exonuclease, Lipase, plasminogen, streptokinase, staphylokinase, urokinase, plasmin, warfarin, monteplase, tenecteplase, reteplase, lanoteplase, pamiteplase, or any other modified tissue type-plasminogen activator, antithrombolytic enzymes derived from leeches such as *Hirudo medicincalis, Hirdinaria manillensis* or *Haementeria ghillanii*, plasminogen activators from the common vampire bat (*Desmodus rotundus*), mutants of plasminogen activators, chimeric plasminogen activators, conjugates of plasminogen activators, and any other plasminogen activators from animal or bacterial origin, and combinations thereof. Dried lysis reagent may be suspended in pellets of trehalose buffer and packaged into tubes as a dry reagent. The dried reagents may then be resuspended in a buffer, added to a 1 to 10 ml volume of blood and incubated for 5 to 20 minutes at room temperature. More specifically, the dried reagent can comprise 1,500 to 4,500 KU Phospholipase A2, 5,000 to 10,000 U Streptokinase, 2 to 10 U Plasminogen, 200 to 3,650 U DNase, 200 to 4,000 U Endonuclease, and 10,000 to 100,000 U Lipase, and optionally one to fifty milligrams of purified (85 to 98% pure) staphylokinase, urokinase, plasmin, warfarin, monteplase, tenecteplase, reteplase, lanoteplase, pamiteplase, or any other modified tissue type-plasminogen activator, antithrombolytic enzymes derived from leeches such as *Hirudo medicincalis, Hirdinaria manillensis* or *Haementeria ghillanii*, plasminogen activators from the common vampire bat (*Desmodus rotundus*), mutants of plasminogen activators, chimeric plasminogen activators, conjugates of plasminogen activators, and any other plasminogen activators from animal or bacterial origin, and combinations thereby.

One embodiment of the present invention includes concentrating and extracting analytes such as prions, toxins, metabolic markers, cancerous matter, disease state markers, and/or pathogens such as bacteria, virus, and fungi from a volume of blood by introducing a Blood Processing Reagent to expose analytes and/or pathogens in an aggregated blood sample and analyzing the blood sample for the particles and/or pathogens now readily identifiable following extraction from the aggregate. The enzyme based Blood Processing Reagent may comprise plasminogen and streptokinase. The plasminogen and streptokinase may be frozen in coincident relation until the fibrin lysis reagent is needed. The streptokinase then reacts with the plasminogen to form plasmin upon thawing. The plasminogen may be suspended in an aqueous salt solution prior to freezing. Suitable salt solutions may include NaCl, $NaPO_4$ or the like. Suitable detergents include methyl 6-O-(N-heptylcarbamoyl)-α-D-glucopyranoside, Triton X-100, and Saponin. To enhance analysis, nucleic acid from particles and/or pathogens may be amplified via polymerase chain reactions (PCR). As an alternative to freezing, enzyme based Blood Processing Reagent may include dried streptokinase and dried plasminogen as the fibrin lysis reagents. The dried reagents may then be mixed and distributed into disposable test containers. This embodiment may be particularly useful for field-testing in locations where sophisticated laboratory equipment and controls are unavailable.

The enzyme based Blood Processing Reagent treated sample solution may be centrifuged for approximately 20 minutes at 5,000 to 5,500×g at a temperature of 10 to 20° C., the supernatant decanted, and the pellet washed. The pellet may be washed three times with a 10 to 20 mM solution of Ecotine/20 mM HEPES pH 7.7 and/or a 10 to 20 mM solution of sucrose/20 mM HEPES pH 7.7. The resultant sample may then be subjected to nucleic acid extraction methods. Materials and methods for nucleic acid extraction are commercially available. The Blood Processing Reagent may be used to treat whole blood samples for 10 minutes. The sample may then be exposed to various embodiments of the Lyses Reagent or filtered with a 0.22 to 0.45 μm Polyethersulfone (PES) filter unit, optionally washed with 10 to 200 mM Aurintricarboxylic Acid, subjected again to lyses and nuclease inactivation using a solution comprising 12.5 to 25 mg proteinase K, preferably 0.5-1.6% methyl 6-O-(N-heptylcarbamoyl)-α-D-glucopyranoside or less desirably 1-1.5% SDS (sodium dodecyl sulfate), and 10 to 20 mM sodium citrate buffer pH 7.8 to pH 8.4 may be utilized. Lysate may be eluted from the filter surface by addition of 3.5 to 4.2 M guanidine isothiocyanate pH 6.4 and extracted according to various embodiments of prior art nucleic acid extraction known commonly as the "Boom" method. Optionally dried reagent may be added.

Nuclease inhibitors that can be used in place of or in conjunction with ATA in the materials and methods of the present invention include Ethylene glycol-bis(2-aminoethylether)-N, N,N,N-tetraacetic, Netropsin dihydrochloridem 1,10-Phenanthroline monohydrate, formaurin-dicarboxylic acid, GR144053F, Evans Blue, vanadyl ribonucleoside complexes, and Melittin.

The pathogens, components, or other matter obtained from a sample according to the present methods can be analyzed and identified using any suitable means known in the art. For example, the solution obtained following the above steps may be applied directly to a biosensor device which can capture and detect pathogenic or native disease state markers developed by the animal against pathogens present in its blood. Alternatively, the solution may be applied directly to a liquid chromatography mass spectrometry device which can detect mass signatures associated with the structural components of the pathogens.

The enzyme based Blood Processing Reagent can comprise detergent and salts. The enzyme based Blood Processing Reagent may aid blood element solubilization by introducing 10 to 30 mM Potassium Phosphate at a pH range of 7.8 to 8.0, driving Phospholipase $A_2$ activity by adding 10 to 80 mM Magnesium Chloride as the divalent cation, adding 20 to 150 mM Sodium Chloride, and including 10 to 200 mM Aurintricarboxylic Acid during the DNase incubation process. The enzyme based Blood Processing Reagent may also include 1.0 to 1.2% Triton X-100 or alternatively the reagents may include combining 20 to 35 mM methyl 6-O-(N-heptylcarbamoyl)-α-D-glucopyranoside and 0.05 to 0.1% Saponin or 20 to 35 mM methyl 6-O-(N-heptylcarbamoyl)-α-D-glucopyranoside by itself; and storing the enzymes by using a trehalose buffer. Storing the enzymes is accomplished by using a trehalose buffer in combination with methyl 6-O-(N-heptylcarbamoyl)-α-D-glucopyranoside. The trehalose storage buffer comprises 10 mM Potassium Phosphate, 0.01 to 0.04% Triton X-100, 1 to 5 mM Dithiothreitol, and 0.3 to 0.5 M Trehalose.

In one embodiment, the sample Lyses Reagent used with the invention contains urea. The sample Lyses Reagent is preferably provided in a dried form so as to minimize the downstream sample volumes and obviate the procedure of having to prepare a proteinase K (PK) solution (since a solution comprising PK in 3.5 to 7.0 M urea is not stable for long periods of time of time). The Lyses Reagent can also contain a detergent such as methyl 6-O-(N-heptylcarbamoyl)-α-D-glucopyranoside. This detergent can be dehydrated with the urea and proteinase K and provided in dry form. The detergent helps to disaggregate proteins but does not denature them.

In another embodiment the nuclease present in the enzyme driven Blood Processing Reagent can be used to nick human DNA while bacterial DNA is left intact. The human DNA may then be removed after nucleic acid extraction by any method by using Single Strand Binding Protein immobilized on magnetic beads. PCR inhibition presented by the human DNA found in large volume blood samples extracts can be reduced as evidenced by testing where said human DNA removal produced earlier PCR noise band crossing points and improved sensitivity compared to no human DNA removal (Table 6).

In FIG. 1, a blood draw 30 is performed on a patient. A solution of PBS, pH 7.4 and 1.2% Triton X-100 is added, the blood is vortexed and centrifuged 40 creating pellet 60 in a 15 ml tube 50. Preferably, resins, metal hydroxides, and/or nano materials may be added with the PBS/Triton X-100 solution to capture particles such as bacteria, virus, fungi, cancerous cells, prions, toxins and the like to contribute greater density to these particles. The increase in particle density allows lower speeds to run during centrifugation.

The supernatant is decanted leaving a fibrin aggregate. A fibrin lysis component 70 is added to tube 50 dissolving the fibrin aggregate and leaving pathogens 65 exposed for analysis. Pathogens 65 are vortexed, centrifuged, and subject to lysis to extract the pathogen DNA. The DNA is then replicated 90 and analyzed 100 for the identity of the suspected pathogen.

In an alternative embodiment of the invention, a device would be used to obviate the need for a centrifuge. The device will use flexible electrodes similar to a fish gill to collect particles (such as bacteria, virus, cancerous cells, prions, or toxins). The electrodes will also be used to collect resins and nano materials that have these particles attached to them. The device will resemble a bubble on a surface. An electrical potential will be used to accelerate pathogen capture. The device can be compressed to allow efficient removal of the contents. The device would preferably have the following properties: (1) a rigid base layer and flexible top layer; (2) flexible gills to be mounted on either the top or bottom layer; (3) Strepavidin and hyaluronic acid strands functionalized with bioactive peptides, antibodies, aptomers, molecular imprinted polymers, or metals that attract particles such as bacteria, virus, fungi, toxins, metabolic markers, disease state markers, or chemical agents are to be deposited on the flexible gill electrodes; (4) the flexible layer will have electrodes deposited on it; (5) counter electrodes for the gill electrodes will reside on the opposite side; (6) the average dead volume of the device is 300 micro liters—it is preferred that there is to be no residual material in the device after squeezing out the material from the device; and (7) polyimide will form the flexible portion and the electrodes will be made of Pt, Au, or carbon. The device is preferably used as follows: (1) flow liquid into the device and apply voltage at this time; (2) add chemicals and heat the device; and (3) squeeze out the device to remove all contents. The device is used to prepare a sample for analysis of particles (such as bacteria, virus, cancerous cells, prions, or toxins) using spectrophotometric, mass spectroscopy, antibodies, culture, or nucleic acid-based (e.g. PCR, NASBA, TMA) detection systems.

A filtering device may be used to filter out the particles from blood treated with the Triton X-100/PBS/magnesium solutions with enzymes selected from the group of streptokinase, plasminogen, phospholipase $A_2$, DNase, and lipase. A filtering device may also be used to filter out the particles from blood treated with a combination of methyl 6-O-(N-heptylcarbamoyl)-α-D-glucopyranoside, Saponin, and PBS/magnesium plus enzymes selected from the group of streptokinase, plasminogen, phospholipase $A_2$, DNase, and lipase. After washing away the enzyme and detergent treatment reagents and any residual broken down blood components, the particle is ready for analysis or further processing.

Figure 2:
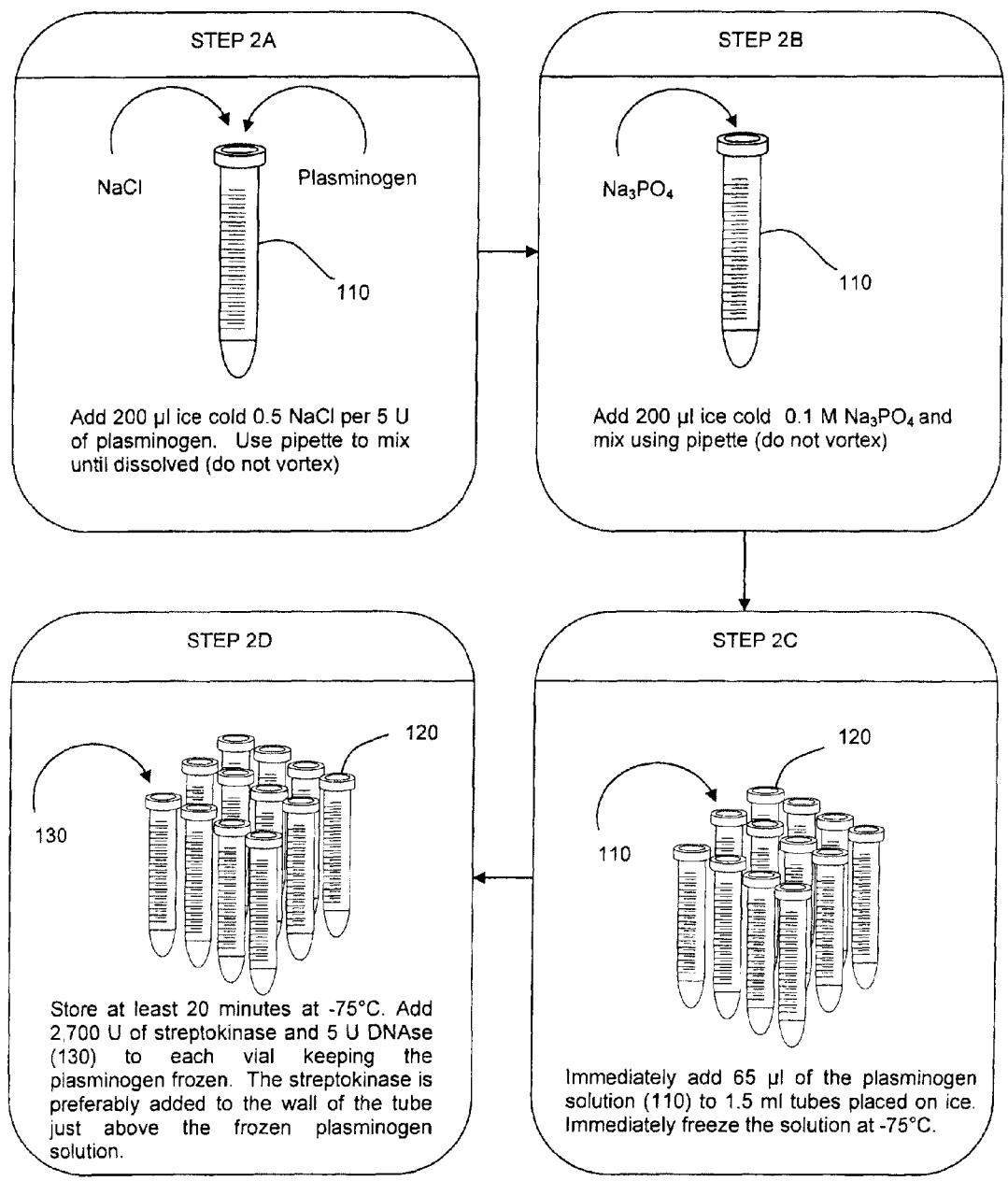
FIG. 2 is a diagrammatic view of the preparation of the fibrin lysis reagent according to Protocol 1 of the invention.

The preparation of the fibrin lysis reagent is shown as Protocol 1 in FIG. 2 wherein NaCl, MnCl, DTT, DNAse, and plasminogen are added to mixing tube 110. Sodium phosphate is then added to mixing tube 110 and the solution is distributed into 1.5 ml reagent tubes 120 placed on ice. The reagent tubes 120 are frozen to −75° C. for approximately 20 minutes. Approximately 2,700 U of streptokinase 130 is added to the wall of reagent tubes 120 just above the frozen plasminogen solution.

Tables 1-4 provide PCR results derived from testing blood samples seeded with encapsulated vegetative avirulent *Bacillus anthracis* were grown according to CDC protocol #CDC.DFA.1.2, stored in 15% glycerol TSB, and frozen at −75° C. Stocks of avirulent *Yersinia pestis* grown in TSB at 37° C., frozen in 15% glycerol TSB, and frozen at −75° C. Bacterial counts were tested at the time of harvest and retested at the time of sample spike.

Figures for average *Bacillus anthracis* CFU per six ml of human blood are derived from post-freezing testing given the large standard deviation encountered in side-by-side post freezing dilution events. No significant cellular death is recognized or expected. A 30% cellular death rate is the highest that is reasonably expected in the worst circumstances. A conservative approach would be to increase all calculated *Bacillus anthracis* CFU by 30%.

Figures for average *Yersinia pestis* CFU per six ml of blood are derived from pre-freezing testing. The low standard deviation of pre-freezing count replicates and concordance with post-freezing testing allows use of the pre-freezing bacteria count numbers. This is a conservative approach that can be utilized given the now predictable results that are derived from storing and diluting this organism.

The present invention reproducibly generates analyte DNA appropriate for PCR testing of pathogens, such as *Bacillus anthracis*, using patient blood samples that are up to 3 months old. Sensitivity is 100% at <10 CFU/ml of human blood when using 6 ml of blood collected in a Becton Dickinson Vacutainer (Tables 1 and 2). This protocol also allows detection of *Yersinia pestis* at 100% sensitivity at <10 CFU/ml for at least one of four oligo sets according to the more limited data gathered for this organism (Table 4). It should be noted that CDC does not consider samples positive for *Y. pestis* unless two oligo sets produce an acceptable PCR signal.

Figure 3:
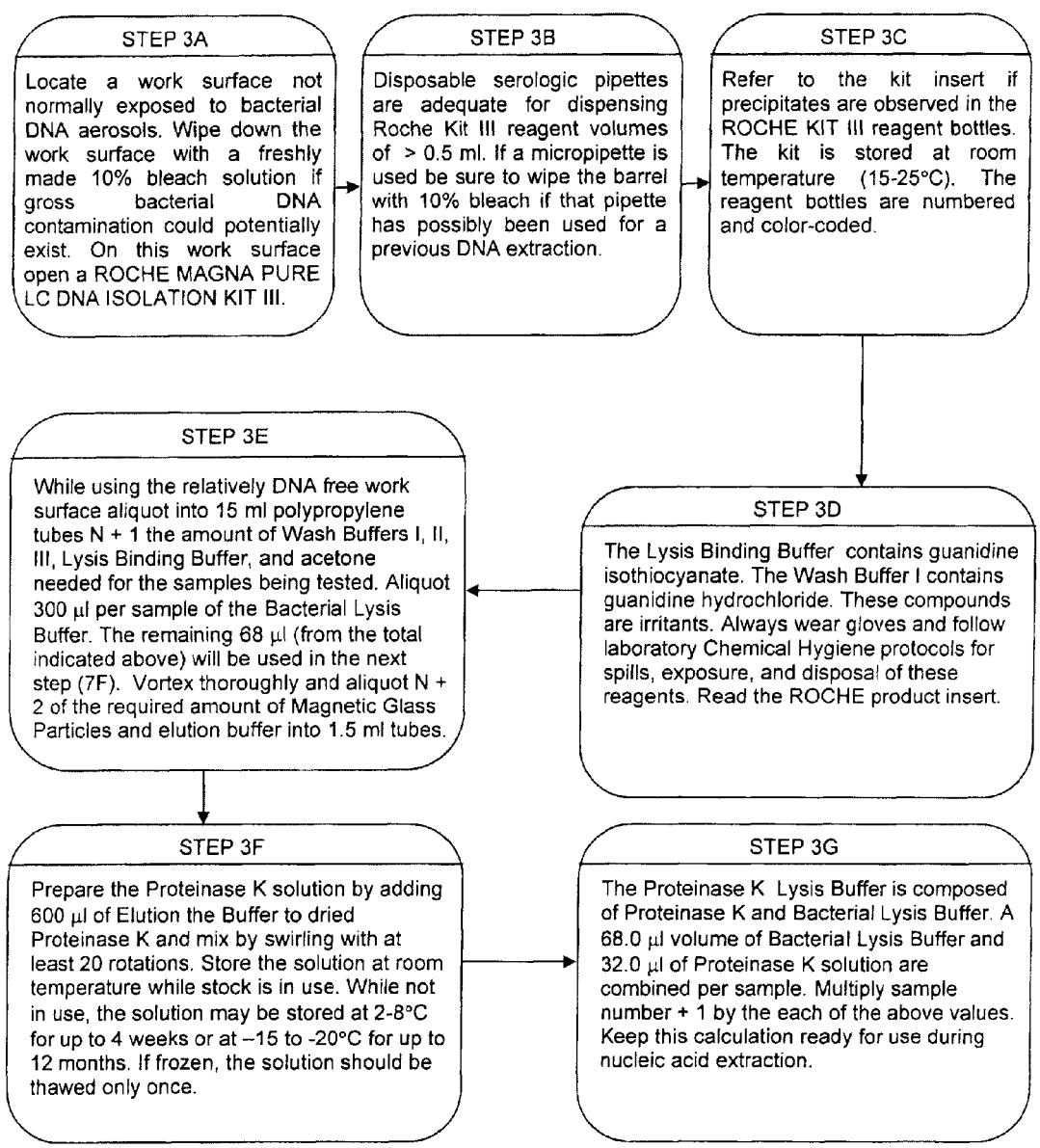
FIG. 3 is a diagrammatic view of the setup of extraction reagents according to Protocol 1 of the invention.
Figure 4:
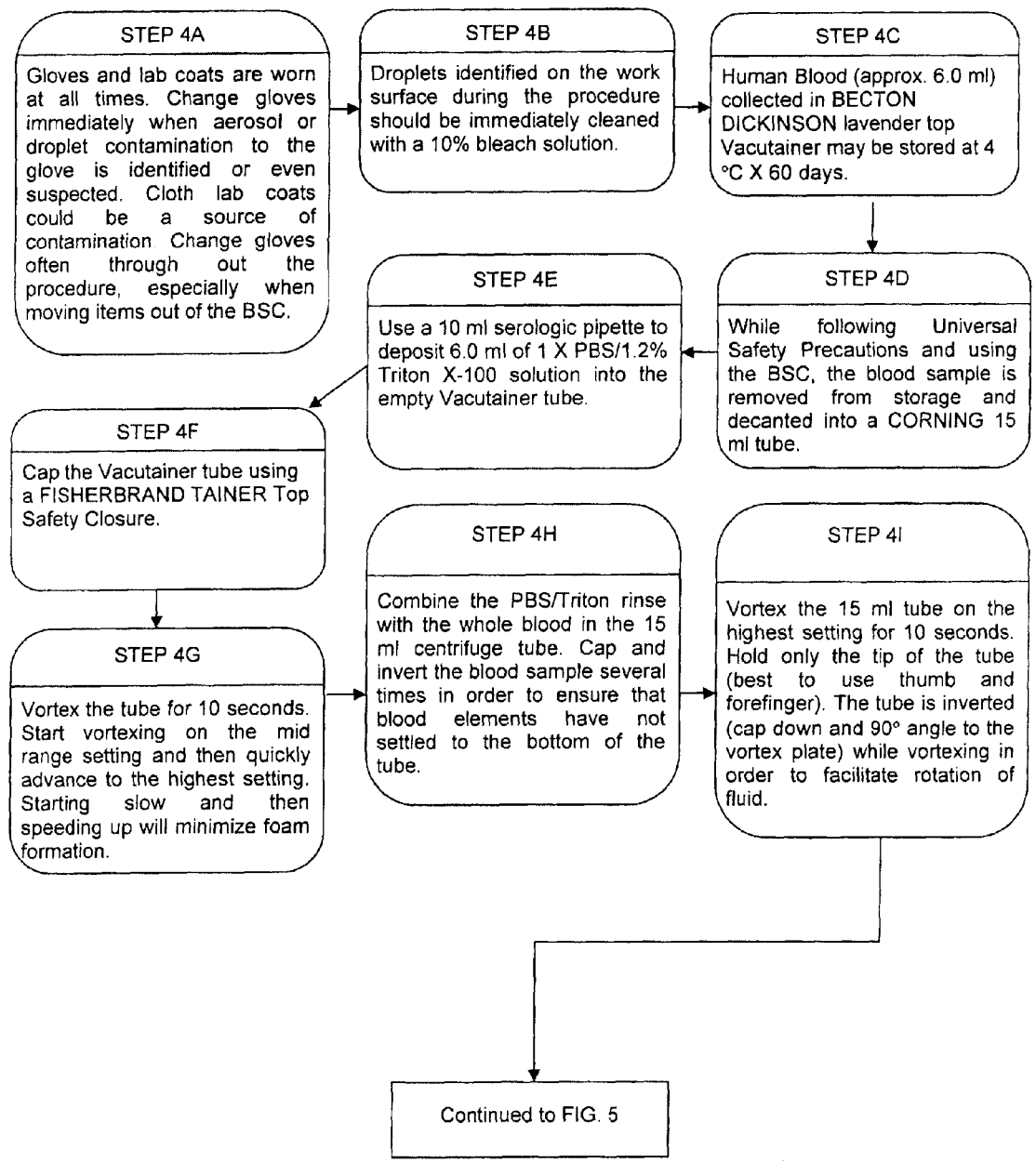
FIGS. 4-5 are diagrammatic views of bacterial recovery and fibrin lysis according to Protocol 1 of the invention.
Figure 5:
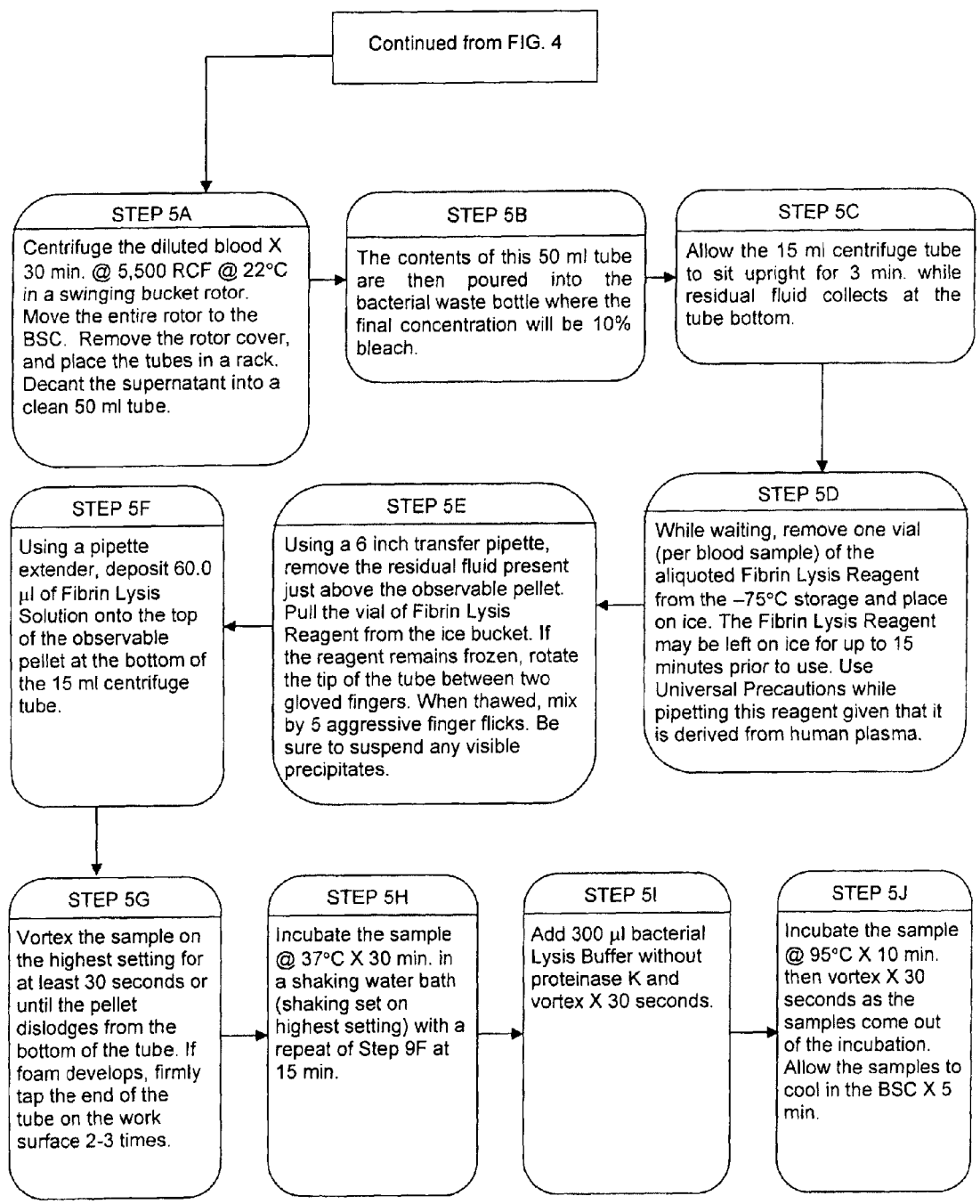
Figure 6:
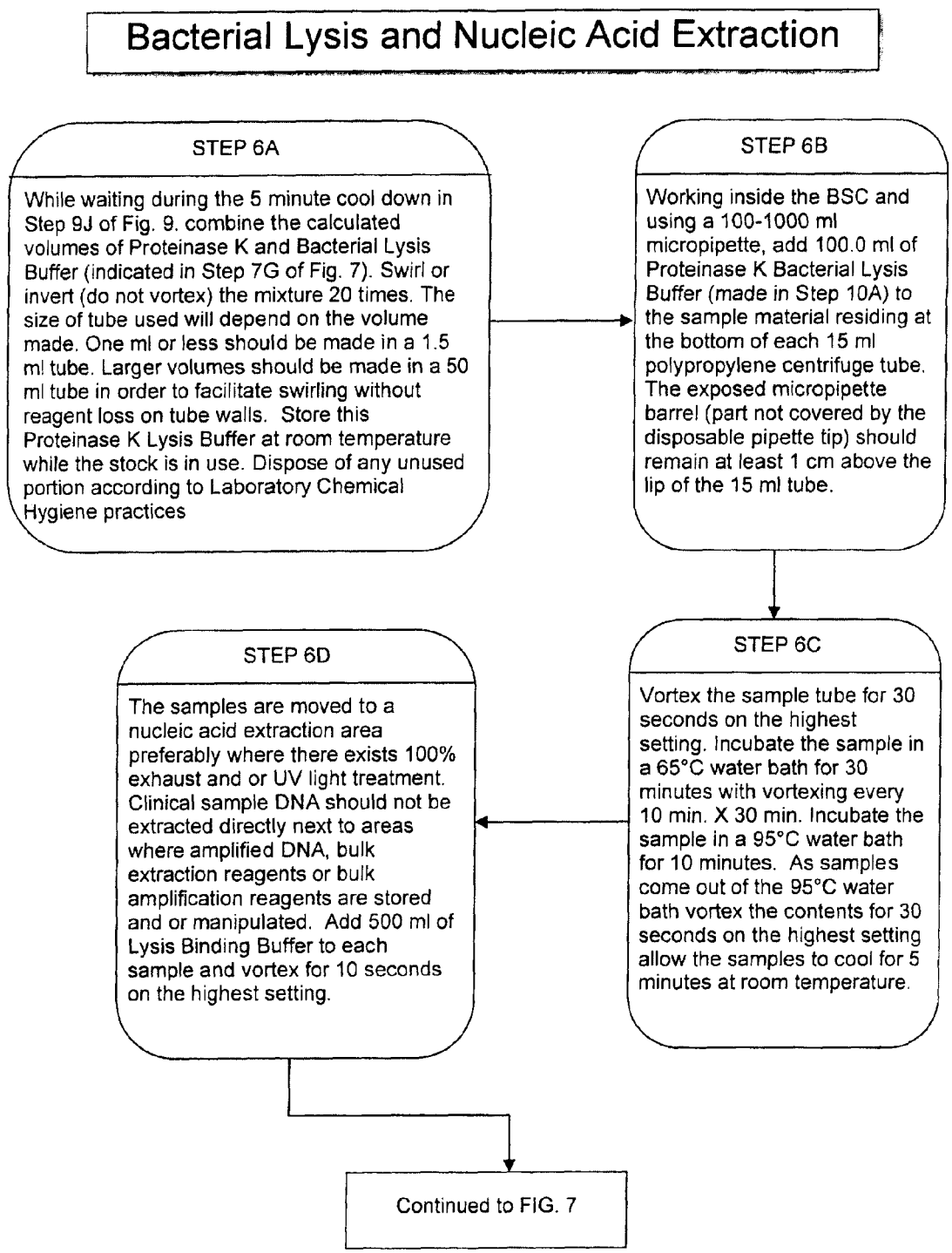
FIG. 6-9 are diagrammatic views of bacterial lysis and nucleic acid extraction according to Protocol 1 of the invention.
Figure 7:
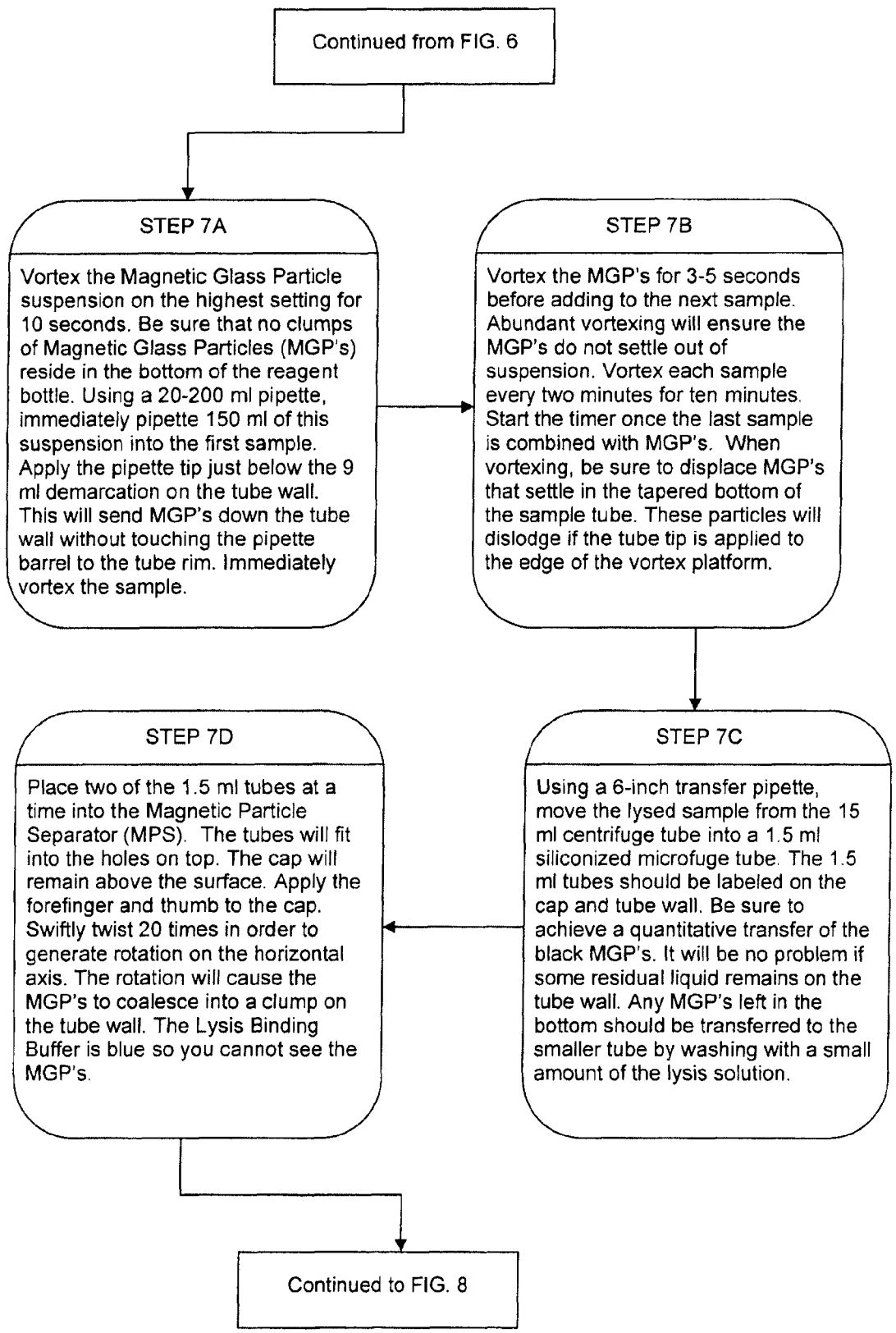
Figure 8:
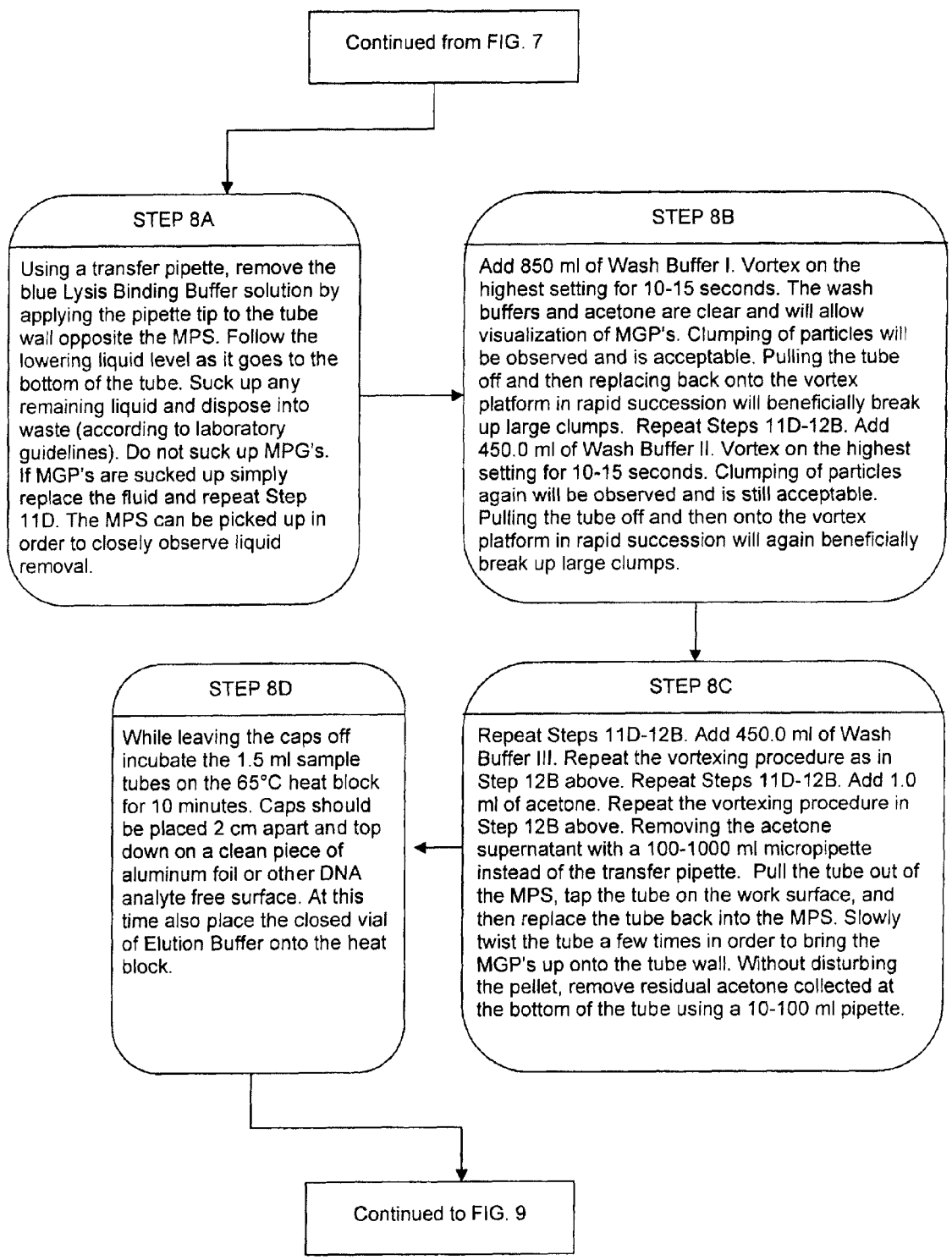
Figure 9:
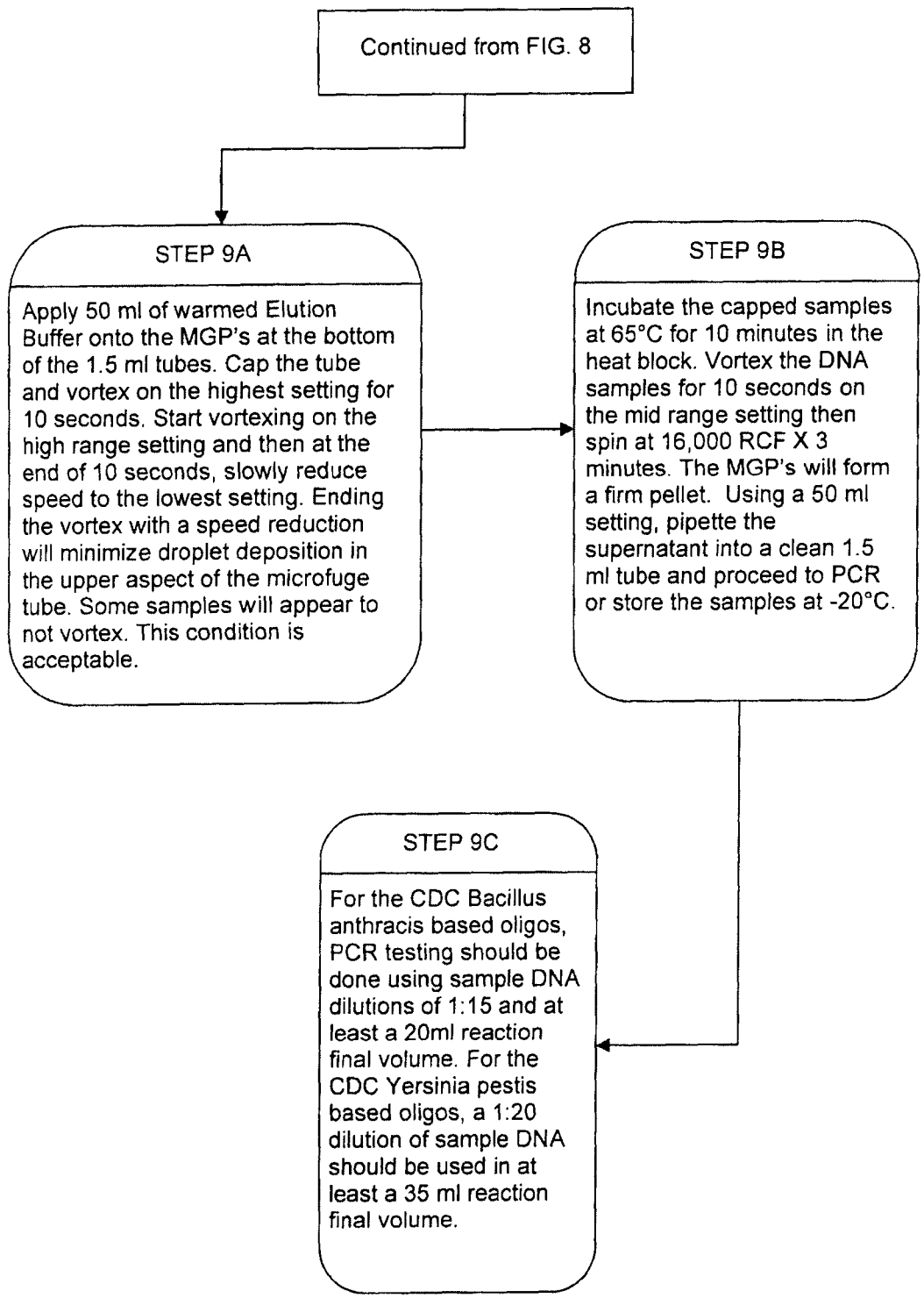

In accordance with Protocol 1, FIG. 3 shows a preferred method of the setup of extraction reagents according to the invention. FIGS. 4-5 show a method of bacterial recovery and fibrin lysis according to the invention. FIGS. 6-9 show a preferred method of bacterial lysis and nucleic acid extraction according to the invention.

In an alternative embodiment, as shown in FIGS. 10-12b, the individual enzymes of streptokinase and plasminogen are made into dried powders, mixed, then distributed to disposable tubes. In another embodiment, Phospholipase $A_2$, plasminogen, DNase or Endonuclease, and lipase are suspended and dried in pellets of trehalose buffer. Although Phospholipase $A_2$ is preferred, any enzyme that will destroy nuclear membrane while keeping bacterial cell wall or viral coats intact may also be used. Streptokinase is likewise suspended and dried in pellets of trehalose buffer. At least one pellet of the plasminogen and one pellet of the streptokinase are packaged into tubes as dried reagents.

Dried reagents of the invention can be resuspended in a 10 ml buffer solution comprising 10 to −30 mM Potassium Phosphate, 10 to 80 mM Magnesium Chloride, 20 to 150 mM Sodium Chloride, 10 to 200 mM Aurintricarboxylic Acid and 1.0 to 1.2% Triton X-100. Aurintricarboxylic Acid is evidenced to provide a level of protection to bacterial nucleic acid without impeding human DNA digestion. The use of Aurintricarboxylic Acid is not described in prior methods of human DNA digestion. Methyl 6-O-(N-heptylcarbamoyl)-α-D-glucopyranoside and/or Saponin can be substituted for Triton X-100. In one embodiment, the methyl 6-O-(N-heptylcarbamoyl)-α-D-glucopyranoside is used at 20 to 35 mM and the saponin is used at 0.05 to 0.19 concentration. The methyl 6-O-(N-heptylcarbamoyl)-α-D-glucopyranoside is stored with the phospholipase $A_2$, plasminogen, DNase I, and lipase in a Trehalose storage buffer. Substitution of the Triton X-100 with the methyl 6-O-(N-heptylcarbamoyl)-α-D-glucopyranoside and/or saponin solution allows for the efficient activity of Phospholipase $A_2$, provides the action of breaking up protein aggregates without denaturation, and is more genial to bacterial walls than Triton X-100. Use of Saponin with methyl 6-O-(N-heptylcarbamoyl)-α-D-glucopyranoside in this combination is not described in the prior art. The Trehalose storage buffer can comprise 10 mM Potassium Phosphate pH 7.4, 0.01 to 0.04% Triton X-100, 1 to 5 mM Dithiothreitol, and 0.3 to 0.5 Trehalose. The buffer and enzyme mix are then immediately combined with a 10 ml blood sample, which may be scaled down to 1 ml. The sample is then incubated at room temperature for 5 to 10 minutes. The aforementioned components aide blood element solubilization through minimizing certain particulates that would otherwise clog filters, impair biosensors or mass spectrometry devices, and impede nucleic acid extraction. Solubilization occurs while human DNA is processed and as viral and/or bacterial DNA remain intact.

In accordance with Protocol 2 and 4, a preferred enzyme based Blood Processing Reagent combination is comprised of Streptokinase, Plasminogen, DNase or Endonuclease, Phospholipase $A_2$, and Lipase. Alternatively, an enzyme combination comprising Streptokinase, Plasminogen, DNase or Endonuclease, and Phospholipase $A_2$ may also be used. In another alternative combination, an enzyme combination comprising Streptokinase, Plasminogen, and DNase or Endonuclease may be used. Alternatively, an enzyme combination comprising DNase, and/or Endonuclease, and/or exonuclease, plus Phospholipase $A_2$ may be used. Alternatively, an enzyme combination comprising DNAse, and/or endonuclease, and/or exonuclease, plus Phospholipase $A_2$, plus Lipase may be used. The biochemical impact on blood matrix disassembly resulting from various combinations of Streptokinase, Plasminogen, DNase, and Phospholipase $A_2$ is described in FIG. 14.

Figure 10A:
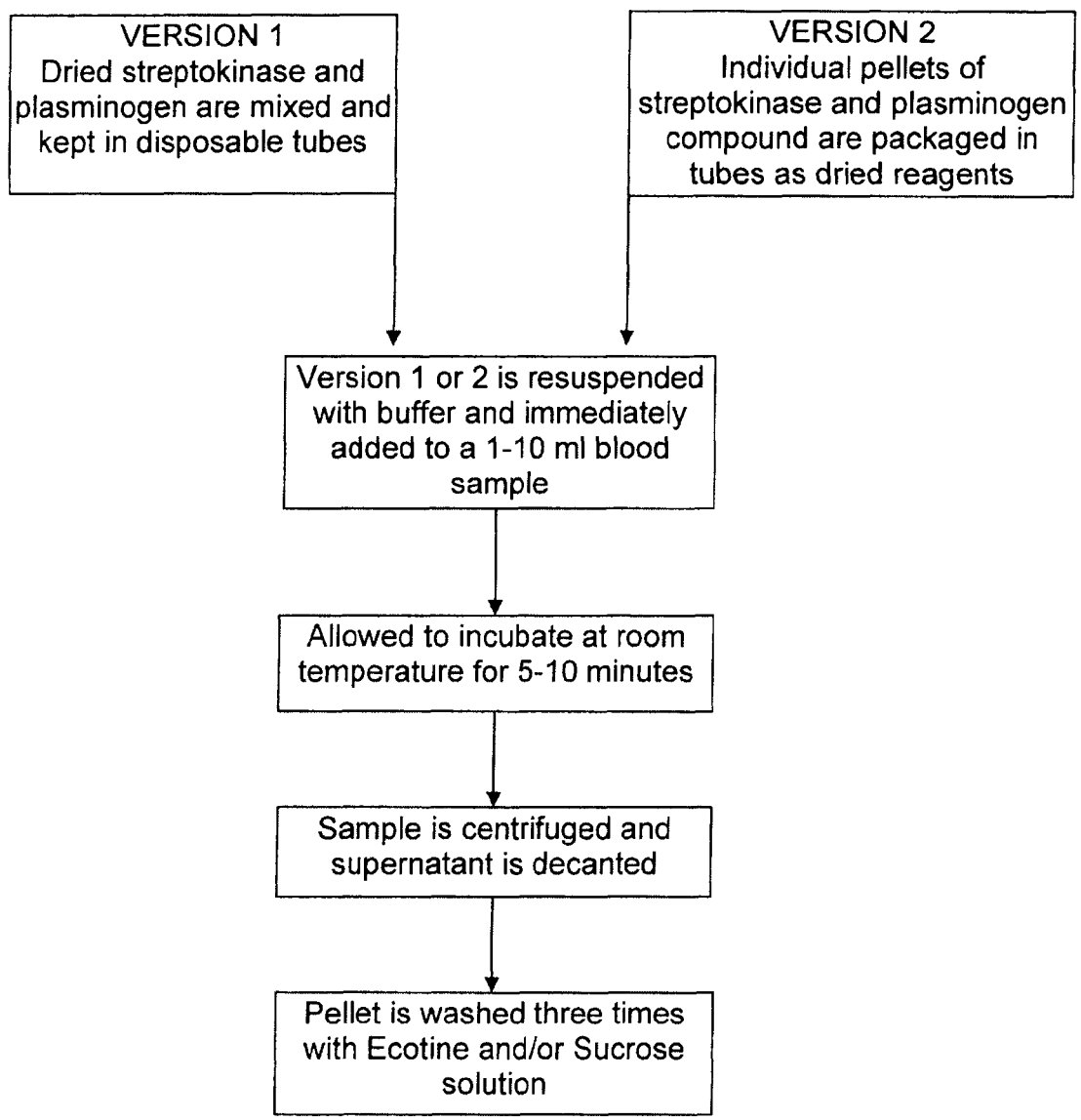
FIG. 10A is a diagrammatic view of the steps of extracting reagents according to Protocol 2 of the invention.
Figure 10B:
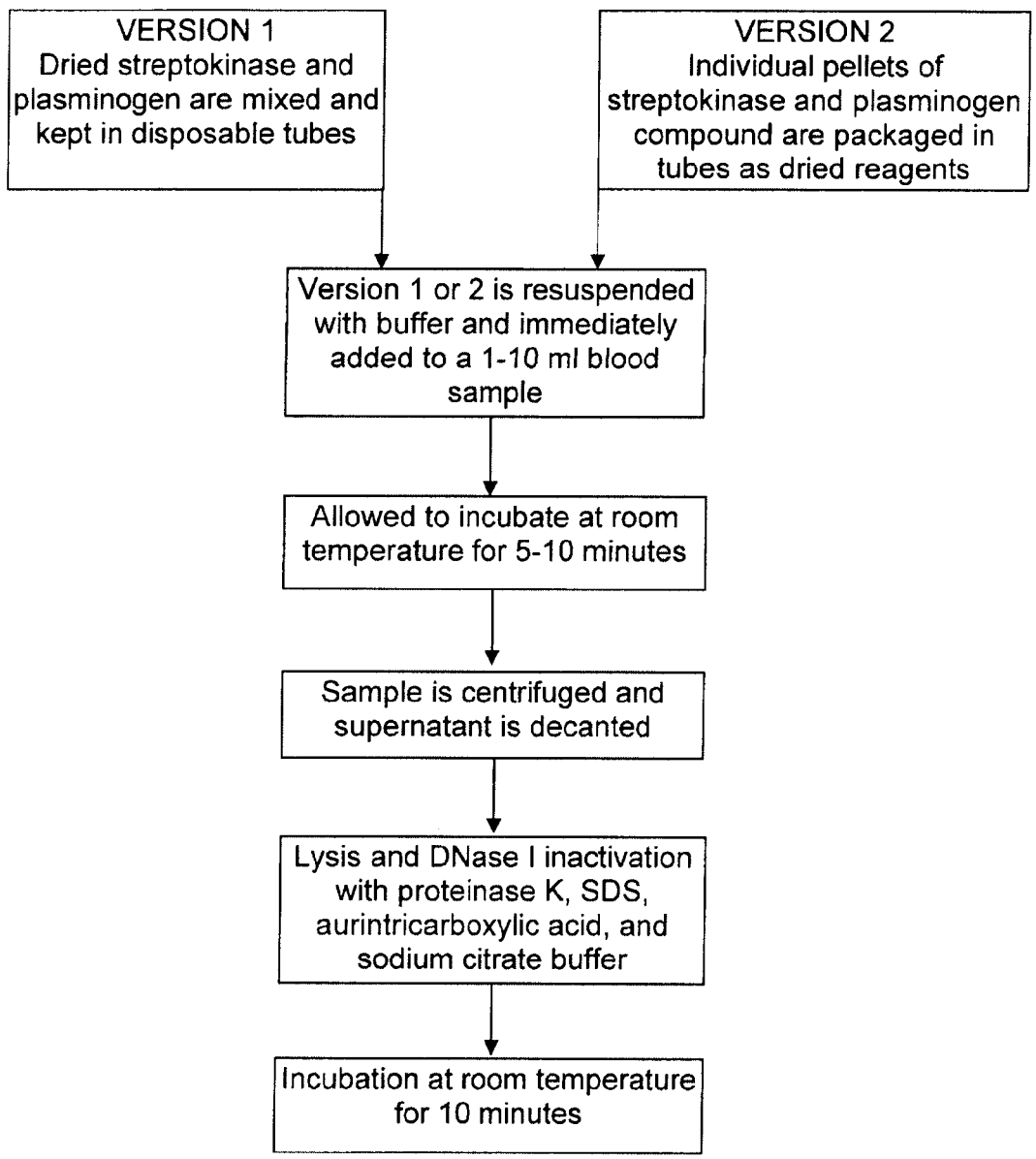
FIG. 10B is a diagrammatic view of the steps of extracting reagents according to Protocol 2 of the invention.

As shown in FIG. 10 with Protocol 2, the sample is centrifuged for a period of 20 minutes at 5,000 to 5,500×g at a temperature between 10 to 22° C. after incubation. The supernatant is then decanted and the pellet washed three times with a 10 to 20 mM solution of Ecotine/20 mM HEPES pH 7.7 and/or a 20 to 30 mM solution of Sucrose/20 mM HEPES pH 7.7. The pellet is then heated to 90° C., centrifuged×5 minutes at 13.00 RCF, and the supernatant is used for PCR analysis.

Alternatively after incubation, the Protocol 2 sample is centrifuged in similar fashion and the supernatant decanted, followed by sample lysis and DNase or Endonuclease inactivation using 12.5 to 25 mg Proteinase K, 1 to 1.5% Sodium Dodecyl Sulfate (SDS), 10 to 200 mM Aurintricarboxylic Acid and 10-20 mM Sodium Citrate buffer pH 7.8 to pH 8.4. The sample is allowed to incubate at room temperature for 10 minutes. The digested sample may then be applied to any commercially available nucleic acid extraction method, shown in FIG. 10B.

Figure 11:
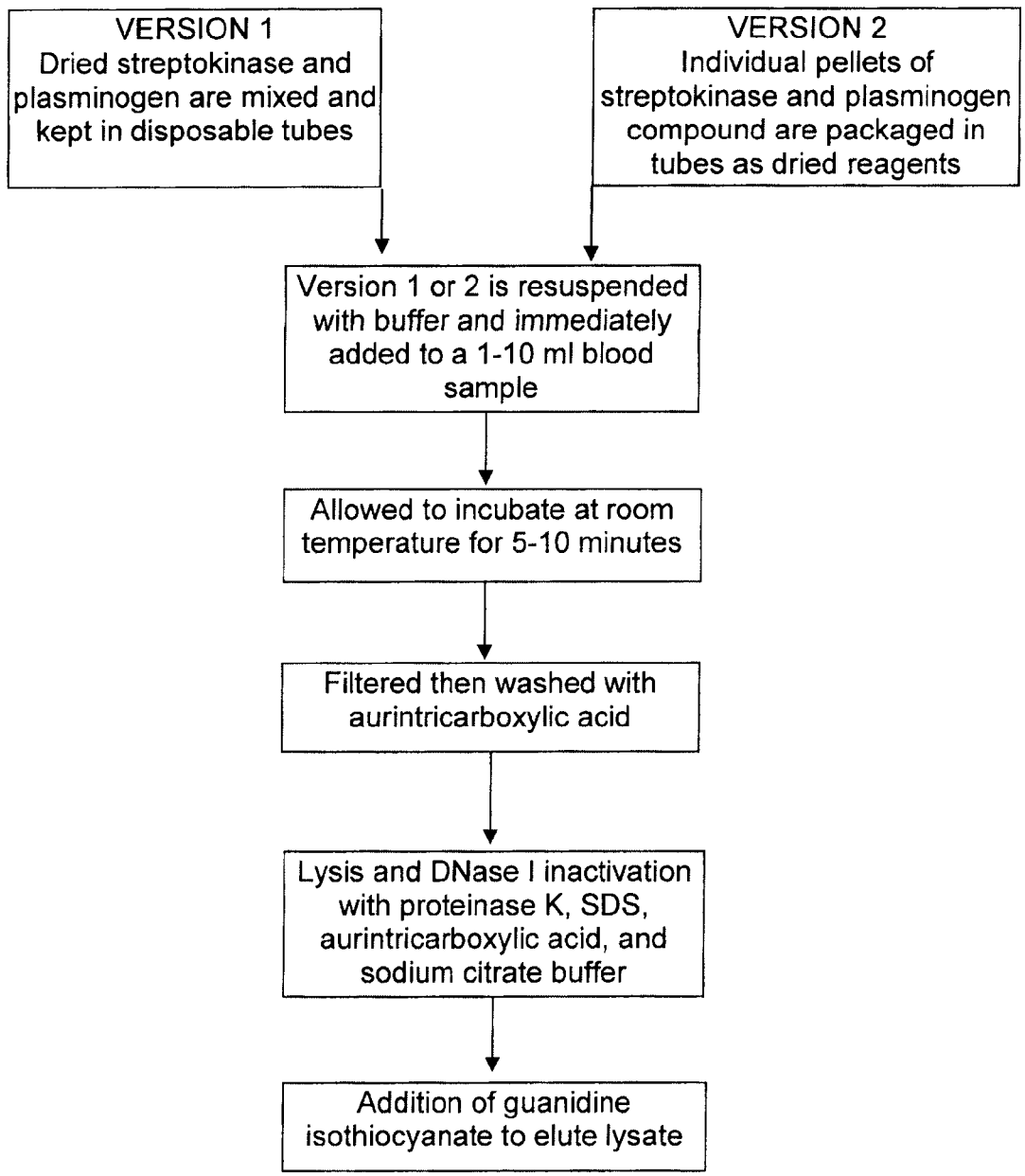
FIG. 11 is a diagrammatic view of the steps of extracting reagents according to Protocol 3 of the invention.

In yet another alternative, referred to as Protocol 3 and depicted in FIG. 11, the sample is filtered with a 0.22 to 0.45 μm filter unit and washed with 10 to 20 ml of 10 to 200 mM Aurintricarboxylic Acid, followed by sample lysis and DNase or Endonuclease inactivation. Sample lysis and DNase or Endonuclease inactivation is accomplished by using 12.5 to 25 mg Proteinase K, 1 to 1.5% SDS, 10 to 200 mM Aurintricarboxylic acid, and 10 to 20 mM Sodium Citrate buffer. The sample is then incubated at room temperature for 10 minutes. Addition of 3.5 to 4.2 M Guanidine Isothiocyanate pH 6.4 is necessary to elute the lysate from the filter surface. The nucleic acid extract may then be further purified using a commercially available method. Data derived from this approach is contained in FIG. 13.

Figure 12A:
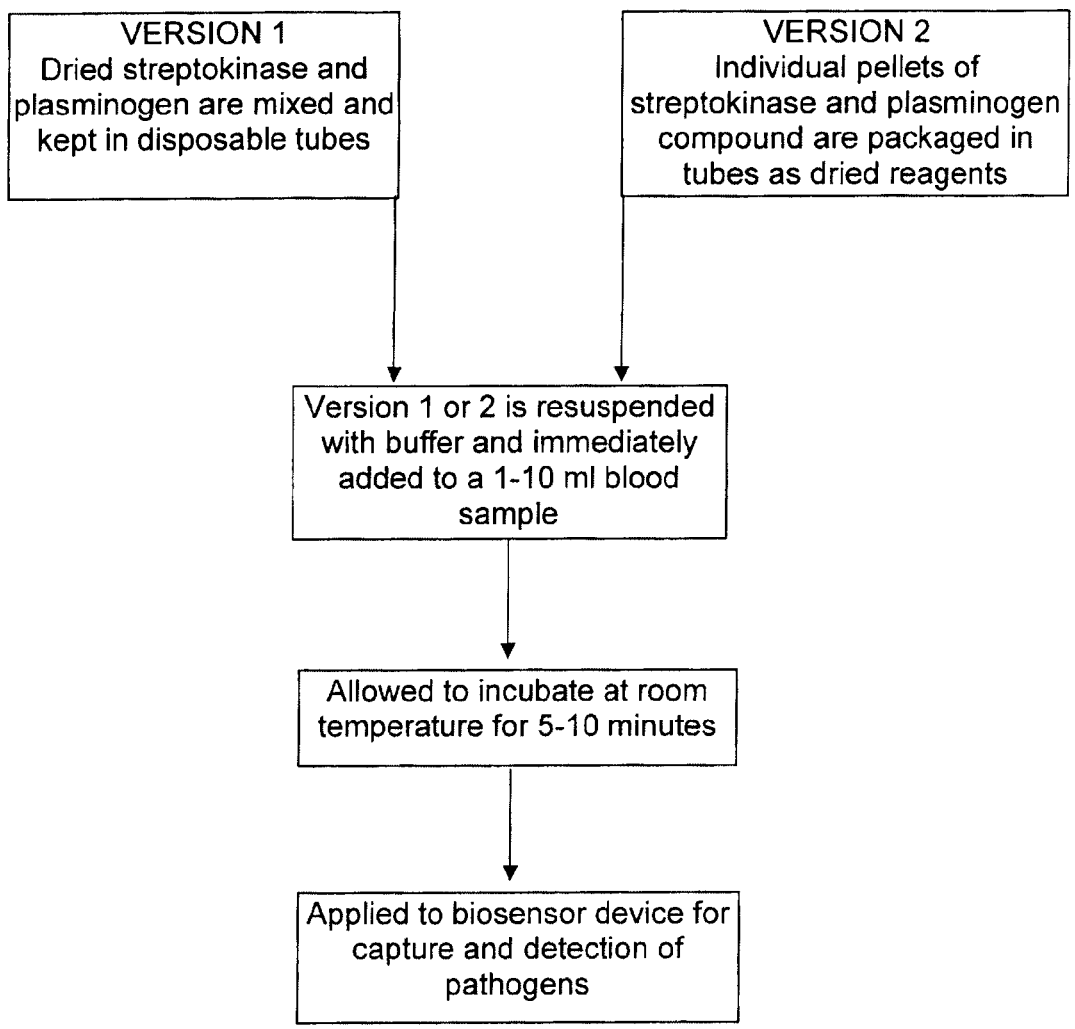
FIG. 12A is a diagrammatic view of the steps of extracting reagents according to Protocol 4 of the invention.

Another alternative, referred to as Protocol 4 and shown as FIG. 12A, the sample is applied directly to a biosensor device that will capture and detect bacteria, virus, fungi, toxins, prions, chemical agents, metabolic markers or native disease state markers developed by the patient's own body in response to these pathogens and agents present in the blood sample.

Figure 12B:
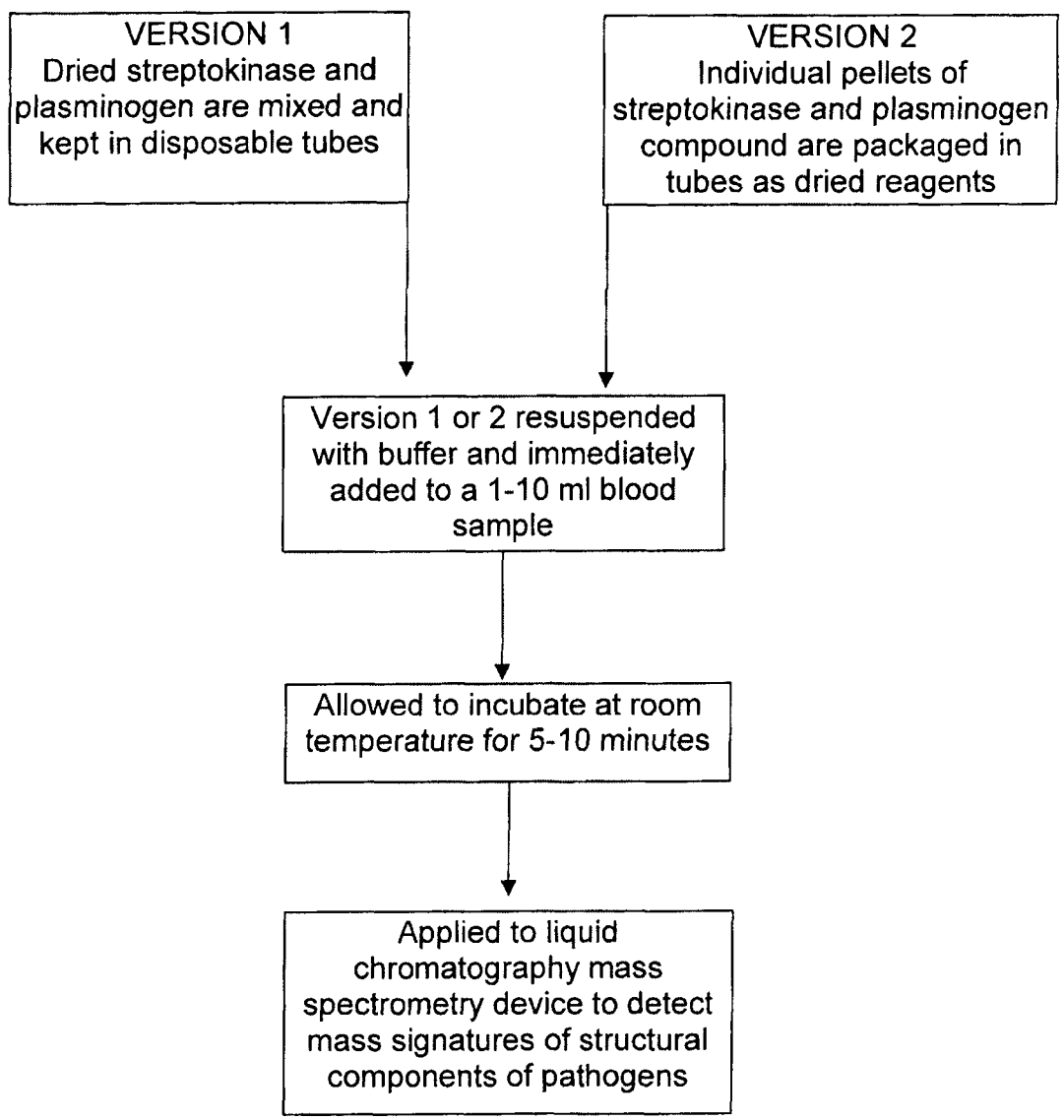
FIG. 12B is a diagrammatic view of the steps of extracting reagents according to Protocol 4 of the invention.
Figure 16:
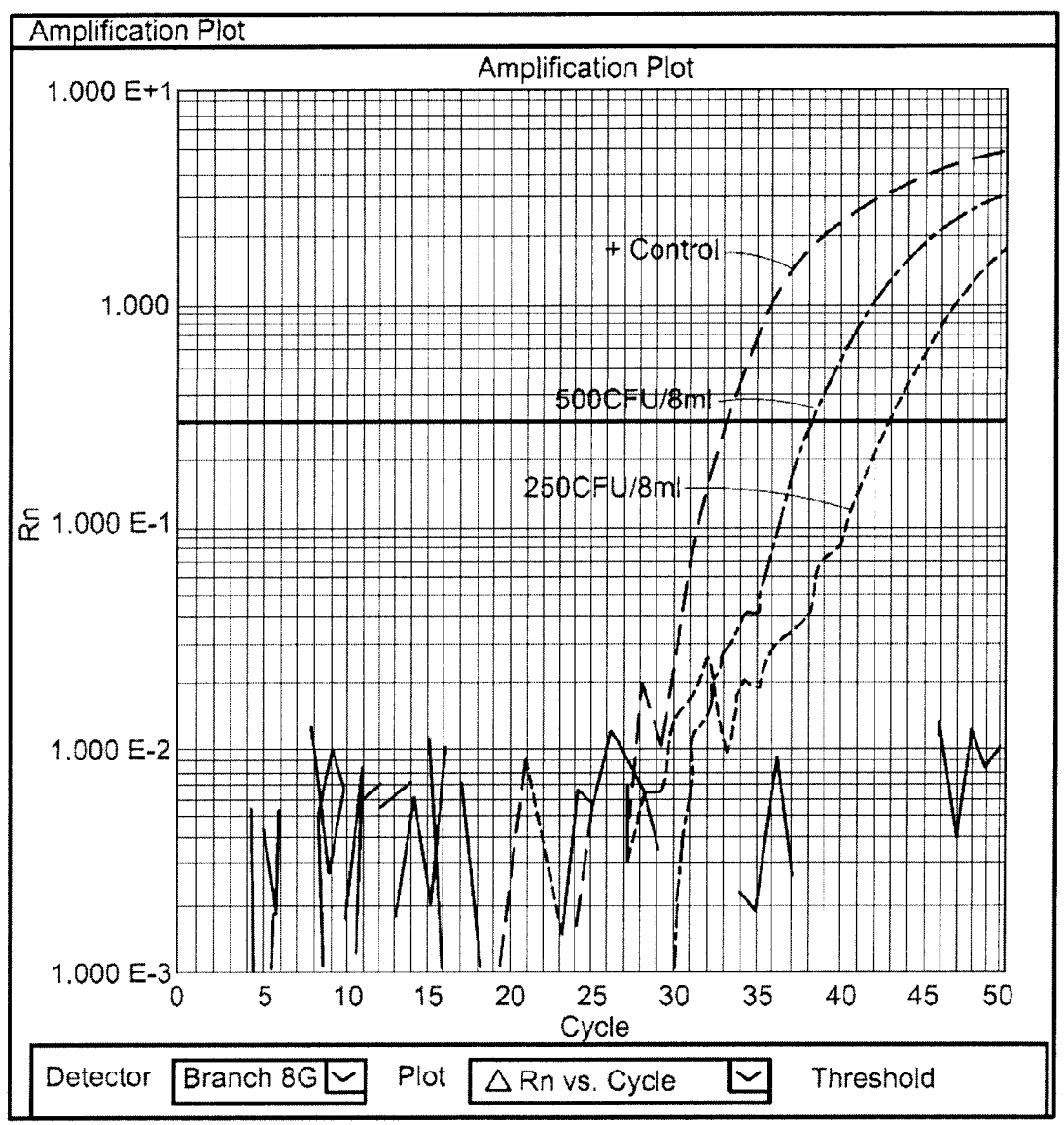
Figure 17:
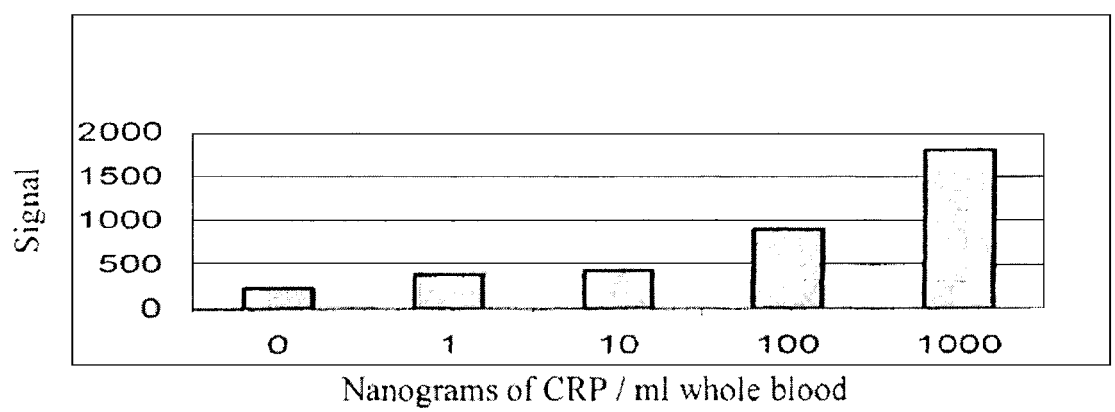

In yet another Protocol 4 alternative shown in FIG. 12B, the sample is applied directly to a liquid chromatography mass spectrometry device that will detect mass signatures of structural components that comprise bacteria, virus, toxins, prions, and chemical agents present in the blood sample or native disease state markers developed by the patient's own body in response to these pathogens and agents present in the blood sample.

The subject invention also concerns a method for preventing or decreasing inhibition of a nucleic acid based pathogen detection assay of a sample by host DNA, such as human DNA, despite the presence of host DNA at concentrations in the sample that would normally inhibit the assay, said method comprising contacting said host DNA with a nuclease and a nuclease inhibitor. Examples of such assays are described herein and in U.S. patent application Ser. No. 10/604,779. In one embodiment, the nuclease is a DNAse, an endonuclease, or an exonuclease. Preferably, the nuclease inhibitor is ATA. Other nuclease inhibitors that can be used include Ethylene glycol-bis(2-aminoethylether)-N,N,N,N-tetraacetic, Netropsin dihydrochloride, 1,10-Phenanthroline monohydrate, formaurin-dicarboxylic acid, GR144053F, Evans Blue, vanadyl ribonucleoside complexes, and Melittin.

The subject invention also concerns materials and methods that can be used for the selective removal of ATA from a composition, such as those containing nucleic acid. Typically, ATA is used in procedures for extracting and purifying RNA from cells, viruses, etc., because of its activity as a ribonuclease inhibitor. Using the claimed invention, the potent ribonuclease inhibitor ATA will always be present during the portion of the nucleic acid extraction process where protein hydrolysis is allowed to proceed at optimal conditions (i.e., with ATA and not chaotrophic salts such as guanidine thiocyanate). The composition can be provided in either solution form or dry, solid form. Preferably, the compositions are provided in a dry solid form to which a liquid or fluid is subsequently added. In an exemplified embodiment, a composition of the invention is used in combination with the lysis reagents described herein.

In one embodiment, a method of the invention comprises contacting a sample that comprises ATA and, optionally, nucleic acid, with a urea composition optionally comprising DTPA (diethylenetriaminepentaacetate). In one embodiment, the sample can comprise any combination of reagents as described in a Lyses Reagent of the invention. A urea/DTPA composition of the invention can be prepared by combining urea with DTPA and optionally EDTA, sodium citrate, and enough of a base, such as sodium hydroxide to achieve pH 8.0 as defined in Table 5. In one embodiment, the urea/DTPA mixture is heated to about 400 to 600° C. for about 1 to 4 hours, dried, ground to a powder, and optionally combined with proteinase K and methyl 6-O-(N-heptylcarbamoyl)-α-D-glucopyranoside prior to addition to the sample in which ATA is to be removed. The urea/DTPA reagent is preferably provided in a dried form so as to minimize the downstream sample volumes and obviate the procedure of having to add proteinase K (PK) in a separate step (since PK is not stable for long periods of time in 6.0 to 7.5 M urea). The ground urea/DTPA reagent is dried under vacuum and added (at 360 mg reagent per ml of blood sample) to blood treated with fibrin lysis reagents described herein. The sample treated with urea/DTPA is incubated 5 to 10 minutes at about 65° C. When samples treated with ATA and a urea/DTPA reagent of the invention are combined with prior art nucleic acid extraction protocols where binding matrices such as silica or other materials that bind nucleic acids in the presence of chaotrophic salts or where precipitation and centrifugation is used, the ATA will not co purify with the nucleic acid extract. In another embodiment, the proteinase K can be inactivated by exposure to temperatures above about 80° C. for 5 to 10 or more minutes, the sample then cooled to below about 40° C., wherein urease is then added to about 1,000 to 100,000 U/ml to break down the urea. The sample can then be applied directly to a nucleic acid array device.

Using the subject methods in conjunction with PCR, 10 CFU *Bacillus anthracis* per 10 ml of blood can be detected. Also, there was no difference in the RT-PCR kinetics derived from PBS samples where 1 ng of MS2 RNA was seeded into nucleic acid extracts made with and without ATA. Also, 1,000 pfu polio cabin III virus/8 ml SPS whole blood was detected by RT-PCR when lysis reagents described herein were combined with the urea/DTPA reagent and protocol described above. By using a urea/DTPA reagent of the invention, ATA that was present prior to the proteinase K digestion step did not have a negative impact on the PCR kinetics using the nucleic acid extracts that were prepared using the subject methods.

In another embodiment, if a sample is not processed with Lyses Reagent, such as those described herein, then a buffer comprising only ATA can be added to the cells as a first step and subsequently treated as outlined above.

In another embodiment, urea can be added to about 6.0 to 7.5 M to an ATA containing sample, and then combined with prior art chaotrophic salt based binding buffers and silica binding matrices, conduct the protocol according to the literature citation or manufacturer specifications with the exception of heating the chaotrophic salt based binding and wash buffer to about 55 to 65° C. prior to use with the sample. The reaction of urea with the ATA plus the combination of this solution with chaotrophic salt at 55 to 65° C. followed by application to a silica based nucleic acid capture matrix allows the selective binding of nucleic acid to the matrix and exclusion of ATA (which is passed out in the capture matrix flow through). It is the combination of reaction with urea and heat that provides for the exclusion of ATA from the silica capture matrix while nucleic acid binds readily. The above described urea/DTPA reagent produced by heating the urea and DTPA combination to between 400 to 600° C. during production eliminates the need for this chaotrophic salt heat step and allows for more complete removal of the ATA.

In another embodiment, blood samples can be treated with ATA containing mixtures described in combination with pathogen capture using bioactive peptides functionalized on hyaluronic acid where the hyaluronic acid in turn acts as a polymeric waveguide. The hyaluronic acid is labeled with biotin via carboxyl groups or amines and the biotin is subsequently removed via dialysis. Strepavidin is cross-linked and the cross-linker is removed via dialysis. The cross-linked strepavidin is added in 100 to 10,000 molar excess to the biotinylated hyaluronic acid and incubated about 4 to 10 hours with or without an applied electrophoretic or dielectrophoretic field. Alternatively, the strepavidin is added in the described ratios, incubated for about 1 to 4 hours with mixing, combined with a photo-activated cross-linking reagent, and cross-linked within as lithography system in order to generate structures positioned within a sample flow path. In this system a calcium release at the site of pathogen capture via bioactive peptide or annealing of RNA species is used to trigger the local conversion of reporter molecule labeled fibrinogen to an insoluble fibrin aggregate at the site of pathogen capture via bioactive peptide or annealing of RNA species upon the matrix of the hyaluronic acid polymeric waveguide. As used herein, bioactive peptides include native and modified non-specific virus binding peptides most optimally, such as lactoferrin or fatty acid modified lactoferrin, and native and modified non-specific bacteria binding peptides, most optimally, such as Cecropin P1, but also including, for example, protamine, Buforin I, Buforin II, Defensin, D-Magainin II, Cecrpin A, Cecropin B, Lectin PA-1, and Tritrpticin. The modified peptides may be altered in terms of amino acid content and include the salts, esters, amides, and acylated forms thereof.

In another embodiment, the bioactive peptides functionalized upon the hyaluronic acid (that is cross linked via biotin and strepavidin) act as pathogen capture moieties. Upon pathogen or biomarker capture, the hyaluronic acid is broken down using 1,000 to 1,000,000 units of hyaluronidase/ml of sample within the device.

In another embodiment, the ATA, magnesium chloride, and potassium phosphate components described in the lysis buffer of the present invention are combined, brought to about pH 9.2 to pH 10 in batches of 100 ml, and heated to boiling until a dry residue forms. The dry residue is ground up, dried further under vacuum, and added to the other enzyme, detergent, and Trehalose components, such as those described herein. In this way the blood can be added directly to dried pellets of Trehalose stabilized reagent where no other liquid or dry components are added for initial blood pretreatment. The dried urea and proteinase K reagent is then added followed by processing as described herein. When this dried reagent system was independently evaluated by government scientists 10 CFU *Yersinia pestis*/ml whole blood was detected via PCR.

The subject invention also concerns compositions comprising ATA that can be used to isolate nucleic acid from a sample. The composition can be provided in either solution form or dry, solid form. Preferably, the compositions are provided in a dry solid form to which a liquid or fluid is subsequently added. *B. anthracis* seeded 8 ml blood sample extracts were tested in the "canonical" SNP (canSNP) analysis system. The 250 CFU/8 ml blood sample gave a strong signal and was easily typed by the Keim Genetics Lab personnel (FIG. 16). Antibody capture of *Salmonella* from whole blood was conducted, followed by PCR and no difference was found compared to capture, wash, and extraction from a PBS/Plasma mixture (Table 7). The CDC RRAT Bioterrorism Lab run by Dr. Rich Meyer has detected 100 CFU *Brucella abortis*/8 ml whole blood using the enzyme based Blood Processing Reagent. USAMRIID Diagnostics Division investigators have detected 10 CFU *Yersinia pestis*/1 ml whole blood using the enzyme based Blood Processing Reagent. The biosensor group at University of Texas at Austin detected 1 ng C-Reactive protein/ml whole blood in a biosensor that would normally never accept a whole blood sample (FIG. 17).

The subject invention also pertains to materials and methods for efficiently removing patient or host (e.g., human) DNA that has been processed by DNAse, endonuclease, or exonuclease while pathogen DNA remains inside intact pathogens. *E. coli* SSB proteins are known in the art and can be used in the methods of the invention. In one embodiment, the SSB is immobilized on magnetic beads. In an exemplified embodiment, the SSB is biotinylated and the solid matrix has avidin or streptavidin attached to the surface, and the SSB is bound to the matrix via the biotin-avidin binding. The sample is then circulated for several minutes at about 37° C. The sample containing the nucleic acid and SSB-matrix is then washed one or more times with a suitable wash buffer, such as 2 mM Tris (pH 8.0). The sample and SSB-matrix is then heated to 90 to 100° C. for a few minutes, the SSB-matrix is separated from the sample and the sample collected. The sample contains purified nucleic acid and can be stored, purified further, or used in PCR, etc.

In one embodiment, a method of the invention comprises contacting a sample that comprises nucleic acid and ATA with a nucleic acid binding matrix. The binding matrix is subsequently contacted with a binding buffer solution comprising a thiocyanate, such as guanidine thiocyanate. After contact with the binding buffer, the binding buffer and sample are removed from contact with the binding matrix, preferably by evacuation of the buffer and sample away from the binding matrix. The binding matrix can optionally be washed one or more times with wash buffer. In one embodiment, blood is collected in a tube containing any commercially available anticoagulant with inversion of the tube 8× immediately post collection. Store the blood at room temperature and process within 14 days post collection. Fresh blood (0-48 hours old) may be best to examine. This is the optimal condition. Refrigerated blood that is 3 months old will also work for instance. Frozen blood may not work if bacteria have lysed via crystallization. Add one volume of whole blood to one tube of Blood Processing Reagent powder (160 mg powder/ml whole blood), vortex on high×15 seconds, and incubate×8 min @ room temperature. Dump one tube of Lysis Reagent powder into the blood sample (350 mg powder/ml whole blood), vortex on high for 15 seconds and incubate in a 65° C. water bath×10 min. Add one volume (equal to volume of blood) of 4.1 M Guanidine Thiocyanate, 9.5% Triton X, 200 mM Tris HCL, pH 6.0 and vortex×5 sec. Contact this mixture with a silica matrix such as a commercially available spin column or magnetic particles coated with silica, or other materials designed to bind nucleic acids in the presence of a chaotrophic salt. Wash the silica matrix with a solution of 4.1 M Guanidine Hydrochloride, 50 mM Tris HCL, pH 6.4. Follow this with a wash using 70% ethanol. Elute the nucleic acid using 2 mM Tris-HCL pH 8.5. The material is now ready for storage or PCR testing.

The examples described herein illustrate procedures for practicing the invention. These examples should not be construed as limiting. All percentages are by weight and all solvent mixture proportions are by volume unless otherwise noted.

TABLE 1

*Bacillus anthracis* Blood Protocol Data Set

| Sample Number | pXO2 Primer/ Probes - Crossing Point on Light Cycler | Genomic Primer/ Probes - Crossing Point on Light Cycler | Ave. Calculated CFU/6 ml of blood | Comments on Sample Type All Samples Tested 2 Days Post Spiking |
|---|---|---|---|---|
| M3200253BA1 | 36.75 | 37.76 | 13.75 | Spiked Positive |
| M3200253BA2 | 36.59 | 37.86 | 13.75 | Spiked Positive |
| M3200253BA3 | 35.97 | 38.10 | 13.75 | Spiked Positive |
| M3200253BA4 | 37.26 | 39.53 | 13.75 | Spiked Positive |
| M3200253BA5 | 35.36 | 40.11 | 13.75 | Spiked Positive |
| M3200253BA6 | 36.35 | 45.19 | 13.75 | Spiked Positive |
| M3200253BA7 | 36.62 | 38.64 | 13.75 | Spiked Positive |
| M3200253BA8 | 37.04 | 39.51 | 13.75 | Spiked Positive |
| M320020BA9 | 0.00 | 0.00 | 0.00 | Blank |
| M/3200226BA1 | 37.16 | 39.35 | 1.38 | Spiked Positive |
| M/3200226BA2 | 36.79 | 40.28 | 1.38 | Spiked Positive |
| M/3200226BA3 | 37.92 | 39.94 | 1.38 | Spiked Positive |
| M/3200226BA4 | 37.49 | 40.16 | 1.38 | Spiked Positive |
| M/3200226BA5 | 39.66 | 40.26 | 1.38 | Spiked Positive |
| M/3200226BA6 | 39.31 | 41.19 | 1.38 | Spiked Positive |
| M/3200226BA7 | 38.48 | 40.73 | 1.38 | Spiked Positive |
| M/320020BA8 | 0.00 | 0.00 | 0.00 | Blank |

TABLE 2

*Bacillus anthracis* Blood Protocol Data Set: Comparison of Blood from Two Different Individuals and Evaluation of Blood Sample Age

| Sample Number | pXO2 Primer/ Probes - Crossing Point on Light Cycler | Genomic Primer/ Probes - Crossing Point on Light Cycler | Ave. Calculated CFU/6 ml of blood | Comments on Sample Type All Samples Extracted 84 Days Post Spiking |
|---|---|---|---|---|
| V210253BA1 | 37.73 | 39.81 | 10.5 | Blood Donor #1 |
| V210253BA2 | 36.74 | 39.05 | 10.5 | Blood Donor #1 |
| V210253BA3 | 36.51 | 37.99 | 10.5 | Blood Donor #1 |
| V210253BA4 | 38.12 | 39.79 | 10.5 | Blood Donor #1 |
| V21020BA5 | 0.00 | 0.00 | 0.00 | Blank |
| M210253BA1 | 37.86 | 39.81 | 2.25 | Blood Donor #2 |
| M210253BA2 | 37.84 | 39.22 | 2.25 | Blood Donor #2 |
| M210253BA3 | 37.24 | 38.52 | 2.25 | Blood Donor #2 |
| M210253BA4 | 38.68 | 39.33 | 2.25 | Blood Donor #2 |
| M21020BA5 | 0.00 | 0.00 | 0.00 | Blank |

TABLE 3

*Bacillus anthracis* Blood Protocol Data Set: Evaluation of Blood Protocol by a Department of Health Laboratorian

| Sample Number | pXO2 Primer/ Probes - Crossing Point on Light Cycler | Genomic Primer/ Probes - Crossing Point on Light Cycler | Ave. Calculated CFU/6 ml of blood | Comments on Sample Type: All Blood Samples Same Batch as in Table 1 |
|---|---|---|---|---|
| M3200256BA1L | 38.81 | 39.93 | 13.75 | Spiked Positive |
| M3200256BA2L | 36.10 | 39.26 | 13.75 | Spiked Positive |
| M/3200223BA3L | 36.77 | 38.58 | 1.38 | Spiked Positive |
| M320020BA4L | 0.00 | 0.00 | 0.00 | Blank |

TABLE 4

*Yersinia pestis* Blood Protocol Data Set

| Sample Number | YP 2 Primer/ Probes - Crossing Point on Light Cycler | YP 9 Primer/ Probes - Crossing Point on Light Cycler | YP 12 Primer/ Probes - Crossing Point on Light Cycler | YP 16 Primer/ Probes - Crossing Point on Light Cycler | Ave. Calculated CFU/6 ml of blood | Comments on Sample Type All Samples Extracted 2 Days Post Spiking |
|---|---|---|---|---|---|---|
| M3180251EYP1 | 0.00 | 0.00 | 0.00 | 37.97 | 12.0 | Spiked Positive |
| M3180251EYP2 | 0.00 | 47.01 | 0.00 | 0.00 | 12.0 | Spiked Positive |
| M3180251EYP3 | 41.56 | 0.00 | 0.00 | 40.29 | 12.0 | Spiked Positive |
| M3180225EYP4 | 0.00 | 0.00 | 0.00 | 38.98 | 24.0 | Spiked Positive |
| M3180225EYP6 | 40.20 | 44.01 | 39.66 | 37.60 | 24.0 | Spiked Positive |
| M3180251FYP7 | 0.00 | 46.15 | 0.00 | 39.79 | 48.0 | Spiked Positive |
| M3180251FYP8 | 40.48 | 43.59 | 41.70 | 35.47 | 48.0 | Spiked Positive |
| M3180251FYP9 | 40.20 | 41.88 | 38.67 | 34.23 | 48.0 | Spiked Positive |
| M318020YP10 | 0.00 | 0.00 | 0.00 | 0.00 | 0.00 | Blank |

TABLE 5

Contents of powdered Urea/DTPA reagent (upon addition of 1 ml sample to 360 mg reagent

| | |
|---|---|
| Urea | 6.0-7.5M |
| Methyl 6-O-(N-heptylcarbamoyl)-α-D-glucopyranoside | 10 to 20 mg/ml |
| Proteinase K | 600-1,000 µg/ml |
| EDTA | 20-70 mM |
| DTPA | 20-70 mM |
| Sodium Citrate | 120 mM |
| Sodium Hydroxide | add to pH 8.0 |

TABLE 6

Assay Reagents Provided by the CDC RRAT Bioterrorism Laboratory

| CFU/6 ml Blood | Sample Number | No HDR Treatment | With HDR Treatment |
|---|---|---|---|
| 20 | 1 | 0.00 | 0.00 |
| 20 | 2 | 0.00 | 0.00 |
| 50 | 3 | 42.11 | 36.68 |
| 50 | 4 | 0.00 | 0.00 |
| 100 | 5 | 40.19 | 36.88 |
| 100 | 6 | 0.00 | 39.24 |
| 200 | 7 | 44.17 | 38.58 |
| 200 | 8 | 0.00 | 36.91 |
| 400 | 9 | 40.45 | 34.48 |
| 400 | 10 | 43.29 | 35.67 |

TABLE 7

Antibody Capture of *Salmonella* from whole blood treated with Blood Processing Reagent; PCR noise band crossing points.

| CFU *Salmonella*/8 ml Sample | Avg. Noise Band Crossing Point PBS/Plasma | Avg. Noise Band Crossing Point Treated Whole Blood |
|---|---|---|
| 1,000 | 31.7 | 31.8 |
| 500 | 32.8 | 32.5 |
| 100 | 33.5 | 33.8 |

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for capturing a particle from a biological sample including the particle, the method comprising:
   (a) contacting the biological sample with:
      (i) 2 to 10 U plasminogen and 5,000 to 10,000 U streptokinase or plasmin produced by combining 2 to 10 U plasminogen and 5,000 to 10,000 U streptokinase,
      (ii) 200 to 3,650 U DNase,
      (iii) 1,500 to 4,500 KU phospholipase $A_2$, and
      (iv) a detergent; and
   (b) capturing the particle,
wherein the particle is a prion, a toxin, a metabolic marker, cancerous matter, a disease state marker, a bacterium, a virus, or a fungus.

2. The method of claim 1, wherein the particle is a bacterium.

3. The method of claim 1, wherein the particle is a fungus.

4. The method of claim 1, wherein the DNase is an endonuclease.

5. The method of claim 1, wherein the method further comprises contacting the biological sample with 10,000 to 100,000 U lipase.

6. The method of claim 1, wherein the capturing the particle comprises filtering the biological sample to extract the particle.

7. The method of claim 6, wherein the filtering comprises filtering the biological sample through a 0.22 to 0.45 mm filter unit.

8. The method of claim 7, wherein the filter unit is a Polyethersulfone (PES) filter unit.

9. The method of claim 1, wherein the biological sample is blood.

10. The method of claim 1, wherein the biological sample is a fibrin aggregate.

11. The method of claim 6, wherein the method further comprises:
   contacting the extracted particle with proteinase K, thereby producing a lysate;
   eluting the lysate from the filter surface; and
   extracting a nucleic acid from the lysate.

12. The method of claim 11, wherein the method further comprises:
   amplifying the nucleic acid by polymerase chain reaction (PCR).

13. The method of claim 1, wherein the capturing the particle comprises centrifuging the biological sample to extract the particle.

* * * * *